(12) United States Patent
Purdy et al.

(10) Patent No.: US 10,660,656 B2
(45) Date of Patent: May 26, 2020

(54) OSTEOTOME WITH A DISTAL PORTION FOR SIMULTANEOUS ADVANCEMENT AND ARTICULATION

(71) Applicant: DFine, Inc., South Jordan, UT (US)

(72) Inventors: Craig Purdy, Sunnyvale, CA (US); Dan Balbierz, Redwood City, CA (US)

(73) Assignee: DFine, Inc., South Jordan, UT (US)

( * ) Notice: Subject to any disclaimer, the term of this patent is extended or adjusted under 35 U.S.C. 154(b) by 166 days.

(21) Appl. No.: 15/862,441

(22) Filed: Jan. 4, 2018

(65) Prior Publication Data

US 2018/0193036 A1    Jul. 12, 2018

Related U.S. Application Data

(60) Provisional application No. 62/443,371, filed on Jan. 6, 2017.

(51) Int. Cl.
| | | |
|---|---|---|
| *A61B 17/16* | (2006.01) | |
| *A61B 17/34* | (2006.01) | |
| *A61B 17/32* | (2006.01) | |
| *A61B 17/00* | (2006.01) | |

(52) U.S. Cl.
CPC ...... *A61B 17/1613* (2013.01); *A61B 17/1671* (2013.01); *A61B 17/32* (2013.01); *A61B 17/320016* (2013.01); *A61B 17/3472* (2013.01); *A61B 2017/003* (2013.01); *A61B 2017/00309* (2013.01); *A61B 2017/00318* (2013.01)

(58) Field of Classification Search
CPC .. A61B 17/16; A61B 17/1613; A61B 17/1671
See application file for complete search history.

(56) References Cited

U.S. PATENT DOCUMENTS

| | | |
|---|---|---|
| 2,688,329 A | 9/1954 | Wallace |
| 3,140,623 A | 7/1964 | Hoose |
| 3,228,400 A | 1/1966 | Armao |
| 3,503,385 A | 3/1970 | Stevens |
| 3,625,200 A | 12/1971 | Muller |
| 3,664,344 A | 5/1972 | Bryne |
| 3,692,465 A | 9/1972 | Cohn et al. |

(Continued)

FOREIGN PATENT DOCUMENTS

| | | |
|---|---|---|
| CA | 2785207 | 7/2011 |
| CN | 88203061 | 11/1988 |

(Continued)

OTHER PUBLICATIONS

US 7,063,700 B2, 06/2006, Michelson (withdrawn)

(Continued)

*Primary Examiner* — Christopher J Beccia
(74) *Attorney, Agent, or Firm* — Stoel Rives LLP

(57) ABSTRACT

Medical devices for creating or expanding a cavity within bone of a patient are disclosed. In some circumstances, a medical device, such as an osteotome is designed to facilitate simultaneous advancement and articulation of a distal portion of the osteotome. Simultaneous advancement and articulation of the distal portion may reduce one or more forces on the distal portion of the osteotome relative to other methods in which advancement and articulation are separated in time, thereby decreasing the risk of breakage or other damage to the osteotome.

17 Claims, 12 Drawing Sheets

(56) References Cited

U.S. PATENT DOCUMENTS

| | | |
|---|---|---|
| 3,794,039 A | 2/1974 | Kollner et al. |
| 3,908,637 A | 9/1975 | Doroshow |
| 4,033,331 A | 7/1977 | Guss et al. |
| 4,131,597 A | 12/1978 | Bluethgen et al. |
| 4,236,520 A | 12/1980 | Anderson |
| 4,276,880 A | 7/1981 | Malmin |
| 4,294,251 A | 10/1981 | Grennwald et al. |
| 4,337,773 A | 7/1982 | Raftopoulos et al. |
| 4,386,717 A | 6/1983 | Koob |
| 4,399,814 A | 8/1983 | Pratt, Jr. et al. |
| 4,411,266 A | 10/1983 | Cosman |
| 4,456,017 A | 6/1984 | Miles |
| 4,473,077 A | 9/1984 | Noiles |
| 4,476,861 A | 10/1984 | Dimakos et al. |
| 4,578,061 A | 3/1986 | Lemelson |
| 4,586,923 A | 5/1986 | Gould et al. |
| 4,595,006 A | 6/1986 | Burke et al. |
| 4,619,263 A | 10/1986 | Frisbie et al. |
| 4,627,434 A | 12/1986 | Murray |
| 4,641,654 A | 2/1987 | Samson et al. |
| 4,653,489 A | 3/1987 | Tronzo |
| 4,668,295 A | 5/1987 | Bajpai |
| 4,719,968 A | 1/1988 | Speros |
| 4,722,948 A | 2/1988 | Sanderson |
| 4,731,054 A | 3/1988 | Billeter et al. |
| 4,742,817 A | 5/1988 | Kawashima et al. |
| 4,747,840 A | 5/1988 | Ladika et al. |
| 4,748,969 A | 6/1988 | Wardle |
| 4,784,638 A | 11/1988 | Ghajar et al. |
| 4,795,602 A | 1/1989 | Pretchel et al. |
| 4,842,603 A | 6/1989 | Draenert |
| 4,843,112 A | 6/1989 | Gerhart et al. |
| 4,846,814 A | 7/1989 | Ruiz |
| 4,865,586 A | 9/1989 | Hedberg |
| 4,869,906 A | 9/1989 | Dingeldein et al. |
| 4,888,366 A | 12/1989 | Chu et al. |
| 4,900,303 A | 2/1990 | Lemelson |
| 4,961,730 A | 10/1990 | Bodicky et al. |
| 4,961,731 A | 10/1990 | Bodicky et al. |
| 4,963,151 A | 10/1990 | Ducheyene et al. |
| 4,969,870 A | 11/1990 | Kramer et al. |
| 4,969,888 A | 11/1990 | Scholten et al. |
| 4,982,730 A | 1/1991 | Royce |
| 5,059,193 A | 1/1991 | Kuslich |
| 4,998,923 A | 3/1991 | Samson et al. |
| 5,004,501 A | 4/1991 | Faccioli |
| 5,017,627 A | 5/1991 | Bonfield |
| 5,046,513 A | 9/1991 | O'Leary et al. |
| 5,049,137 A | 9/1991 | Thompson |
| 5,049,157 A | 9/1991 | Mittelmeier et al. |
| 5,085,861 A | 2/1992 | Gerhart et al. |
| 5,088,991 A | 2/1992 | Weldon |
| 5,116,305 A | 2/1992 | Milder et al. |
| 5,092,891 A | 3/1992 | Kummer et al. |
| 5,103,804 A | 4/1992 | Abele |
| 5,108,404 A | 4/1992 | Scholten et al. |
| 5,112,303 A | 5/1992 | Pudenz et al. |
| 5,114,414 A | 5/1992 | Buchbinder |
| 5,147,334 A | 9/1992 | Moss |
| 5,156,606 A | 10/1992 | Chin |
| 5,163,431 A | 11/1992 | Greip |
| 5,184,757 A | 2/1993 | Giannuzzi |
| 5,188,619 A | 2/1993 | Myers |
| 5,196,201 A | 3/1993 | Larsson et al. |
| 5,197,971 A | 3/1993 | Bonutti |
| 5,211,631 A | 5/1993 | Sheaff |
| 5,231,969 A | 8/1993 | Middleman et al. |
| 5,242,082 A | 9/1993 | Giannuzzi |
| 5,264,214 A | 11/1993 | Rhee et al. |
| 5,266,248 A | 11/1993 | Ohtsuka et al. |
| 5,269,750 A | 12/1993 | Grulke et al. |
| 5,282,821 A | 2/1994 | Donahue |
| 5,284,128 A | 2/1994 | Hart |
| 5,285,795 A | 2/1994 | Ryan et al. |
| 5,295,980 A | 3/1994 | Ersek |
| 5,296,026 A | 3/1994 | Monroe et al. |
| 5,308,342 A | 5/1994 | Sepetka et al. |
| 5,322,064 A | 6/1994 | Lundquist |
| 5,322,505 A | 6/1994 | Krause et al. |
| 5,334,181 A | 8/1994 | Rubinsky et al. |
| 5,336,699 A | 8/1994 | Cooke et al. |
| 5,343,877 A | 9/1994 | Park |
| 5,352,715 A | 10/1994 | Wallace et al. |
| 5,356,629 A | 10/1994 | Sander |
| 5,360,416 A | 11/1994 | Ausherman et al. |
| 5,368,598 A | 11/1994 | Hasson |
| 5,372,587 A | 12/1994 | Hammerslag et al. |
| 5,378,234 A | 1/1995 | Hammerslag et al. |
| 5,380,307 A | 1/1995 | Chee et al. |
| 5,385,563 A | 1/1995 | Groos |
| 5,389,073 A | 2/1995 | Imran |
| 5,425,770 A | 6/1995 | Piez et al. |
| 5,431,168 A | 7/1995 | Webster, Jr. |
| 5,431,639 A | 7/1995 | Shaw |
| 5,437,636 A | 8/1995 | Snoke et al. |
| 5,449,301 A | 9/1995 | Hanna et al. |
| 5,449,351 A | 9/1995 | Zohmann |
| 5,458,597 A | 10/1995 | Edwards et al. |
| 5,480,382 A | 1/1996 | Hammerslag et al. |
| 5,484,424 A | 1/1996 | Cottenceau et al. |
| 5,489,275 A | 2/1996 | Thompson et al. |
| 5,496,330 A | 3/1996 | Bates et al. |
| 5,512,610 A | 4/1996 | Lin |
| 5,514,130 A | 5/1996 | Baker |
| 5,514,137 A | 5/1996 | Coutts |
| 5,531,715 A | 7/1996 | Engelson et al. |
| 5,535,922 A | 7/1996 | Maziarz |
| 5,549,542 A | 8/1996 | Kovalcheck |
| 5,549,679 A | 8/1996 | Kuslich |
| 5,554,114 A | 9/1996 | Wallace et al. |
| 5,571,085 A | 11/1996 | Accisano, III |
| 5,571,088 A | 11/1996 | Lennox |
| 5,574,075 A | 11/1996 | Draemert |
| 5,599,346 A | 2/1997 | Edwards et al. |
| 5,616,121 A | 4/1997 | McKay |
| 5,620,447 A | 4/1997 | Smith et al. |
| 5,620,467 A | 4/1997 | Wagner |
| 5,624,396 A | 4/1997 | McNamara et al. |
| 5,628,771 A | 5/1997 | Mizukawa et al. |
| 5,637,090 A | 6/1997 | McGee |
| 5,637,091 A | 6/1997 | Hakky et al. |
| 5,662,680 A | 9/1997 | Desai |
| 5,681,269 A | 10/1997 | Wilcox et al. |
| 5,681,282 A | 10/1997 | Eggers et al. |
| 5,681,317 A | 10/1997 | Caldarise |
| 5,685,826 A | 11/1997 | Bonutti |
| 5,695,513 A | 12/1997 | Johnson et al. |
| 5,697,536 A | 12/1997 | Eggers et al. |
| 5,697,909 A | 12/1997 | Eggers et al. |
| 5,700,157 A | 12/1997 | Chung |
| 5,704,926 A | 1/1998 | Sutton |
| 5,709,697 A | 1/1998 | Ratcliff et al. |
| 5,725,568 A | 3/1998 | Hastings |
| 5,735,829 A | 4/1998 | Cherian |
| 5,741,320 A | 4/1998 | Thornton et al. |
| 5,766,153 A | 6/1998 | Eggers et al. |
| 5,800,408 A | 9/1998 | Strauss et al. |
| 5,810,804 A | 9/1998 | Gough |
| 5,810,867 A | 9/1998 | Zarbatany et al. |
| 5,820,592 A | 10/1998 | Hammerslag et al. |
| 5,833,632 A | 11/1998 | Jacobsen et al. |
| 5,833,692 A | 11/1998 | Cesarini et al. |
| 5,847,046 A | 12/1998 | Jiang et al. |
| 5,849,028 A | 12/1998 | Chen |
| 5,851,212 A | 12/1998 | Zirps et al. |
| 5,855,577 A | 1/1999 | Murphy-Chutorian et al. |
| 5,858,003 A | 1/1999 | Atala |
| 5,860,952 A | 1/1999 | Quinn |
| 5,860,974 A | 1/1999 | Abele |
| 5,876,373 A | 3/1999 | Giba et al. |
| 5,891,027 A | 4/1999 | Tu |
| 5,902,251 A | 5/1999 | VanHooydonk |
| 5,902,839 A | 5/1999 | Lautenschlager et al. |
| 5,914,356 A | 6/1999 | Erbe |

(56) References Cited

U.S. PATENT DOCUMENTS

| | | |
|---|---|---|
| 5,921,956 A | 7/1999 | Grinberg et al. |
| 5,928,239 A | 7/1999 | Mirza |
| 5,931,829 A | 8/1999 | Burbank et al. |
| 5,944,715 A | 8/1999 | Goble et al. |
| 5,947,964 A | 9/1999 | Eggers |
| 5,972,015 A | 10/1999 | Scribner et al. |
| 5,997,581 A | 12/1999 | Khalili |
| 6,019,765 A | 2/2000 | Thornhill et al. |
| 6,027,487 A | 2/2000 | Crocker |
| 6,030,360 A | 2/2000 | Biggs |
| 6,048,346 A | 4/2000 | Reiley et al. |
| 6,059,739 A | 5/2000 | Baumann |
| 6,063,078 A | 5/2000 | Wittkampf |
| 6,064,902 A | 5/2000 | Haissaguerre |
| 6,066,154 A | 5/2000 | Reiley et al. |
| 6,066,176 A | 5/2000 | Oshida |
| 6,073,051 A | 6/2000 | Sharkey et al. |
| 6,080,801 A | 6/2000 | Draenert et al. |
| 6,099,514 A | 8/2000 | Sharkey et al. |
| 6,106,524 A | 8/2000 | Eggers et al. |
| 6,106,539 A | 8/2000 | Fortier |
| 6,110,155 A | 8/2000 | Baudino |
| 6,123,702 A | 9/2000 | Swanson |
| 6,127,597 A | 10/2000 | Beyar et al. |
| 6,135,999 A | 10/2000 | Fanton et al. |
| 6,146,355 A | 11/2000 | Biggs |
| 6,156,254 A | 12/2000 | Andrews et al. |
| 6,183,435 B1 | 2/2001 | Bumbalough et al. |
| 6,203,507 B1 | 3/2001 | Wadsworth et al. |
| 6,203,574 B1 | 3/2001 | Kawamura |
| 6,228,052 B1 | 5/2001 | Pohndorf |
| 6,228,904 B1 | 5/2001 | Yadav et al. |
| 6,231,569 B1 | 5/2001 | Bek et al. |
| 6,231,615 B1 | 5/2001 | Preissman |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,251,092 B1 | 6/2001 | Qin et al. |
| 6,258,086 B1 | 7/2001 | Ashley et al. |
| 6,270,476 B1 | 8/2001 | Santoianni et al. |
| 6,280,413 B1 | 8/2001 | Clark et al. |
| 6,280,434 B1 | 8/2001 | Kinoshita et al. |
| 6,280,441 B1 | 8/2001 | Ryan |
| 6,280,456 B1 | 8/2001 | Scribner et al. |
| 6,280,473 B1 | 8/2001 | Lemperle et al. |
| 6,283,960 B1 | 9/2001 | Ashley |
| 6,291,547 B1 | 9/2001 | Lyles |
| 6,312,428 B1 | 11/2001 | Eggers |
| 6,312,454 B1 | 11/2001 | Stockel et al. |
| 6,332,894 B1 | 12/2001 | Stalcup et al. |
| 6,348,055 B1 | 2/2002 | Preissman |
| 6,352,533 B1 | 3/2002 | Ellman et al. |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,408,889 B1 | 6/2002 | Komachi |
| 6,409,722 B1 | 6/2002 | Hoey et al. |
| 6,428,894 B1 | 8/2002 | Babich et al. |
| 6,437,019 B1 | 8/2002 | Rusin et al. |
| 6,440,138 B1 | 8/2002 | Reiley et al. |
| 6,447,506 B1 | 9/2002 | Swanson et al. |
| 6,447,514 B1 | 9/2002 | Stalcup et al. |
| 6,464,683 B1 | 10/2002 | Samuelson et al. |
| 6,478,793 B1 | 11/2002 | Cosman et al. |
| 6,479,565 B1 | 11/2002 | Stanley |
| 6,484,904 B1 | 11/2002 | Horner et al. |
| 6,506,217 B1 | 1/2003 | Arnett |
| 6,511,471 B2 | 1/2003 | Rosenman et al. |
| 6,524,296 B1 | 2/2003 | Beals |
| 6,565,588 B1 | 5/2003 | Clement et al. |
| 6,575,969 B1 | 6/2003 | Rittman et al. |
| 6,575,978 B2 | 6/2003 | Peterson et al. |
| 6,576,249 B1 | 6/2003 | Gendler et al. |
| 6,582,446 B1 | 6/2003 | Marchosky |
| 6,592,559 B1 | 7/2003 | Pakter et al. |
| 6,599,961 B1 | 7/2003 | Pienkowski et al. |
| 6,620,162 B2 | 7/2003 | Kuslich et al. |
| 6,602,248 B1 | 8/2003 | Sharps et al. |
| 6,607,544 B1 | 8/2003 | Boucher et al. |
| 6,613,054 B2 | 9/2003 | Scribner et al. |
| 6,622,731 B2 | 9/2003 | Daniel et al. |
| 6,623,448 B2 | 9/2003 | Slater |
| 6,638,268 B2 | 10/2003 | Niazi |
| 6,641,587 B2 | 11/2003 | Scribner et al. |
| 6,645,213 B2 | 11/2003 | Sand et al. |
| 6,663,647 B2 | 12/2003 | Reiley et al. |
| 6,676,665 B2 | 1/2004 | Foley et al. |
| 6,679,886 B2 | 1/2004 | Weikel et al. |
| 6,689,823 B1 | 2/2004 | Bellare et al. |
| 6,692,532 B1 | 2/2004 | Healy et al. |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,090 B1 | 5/2004 | Cragg et al. |
| 6,740,093 B2 | 5/2004 | Hochschuler et al. |
| 6,743,239 B1 | 6/2004 | Kuehn et al. |
| 6,746,451 B2 | 6/2004 | Middleton et al. |
| 6,752,863 B2 | 6/2004 | Lyles et al. |
| 6,753,007 B2 | 6/2004 | Haggard et al. |
| 6,770,079 B2 | 8/2004 | Bhatnagar et al. |
| 6,814,734 B2 | 11/2004 | Chappuis et al. |
| 6,814,736 B2 | 11/2004 | Reiley et al. |
| 6,818,001 B2 | 11/2004 | Wulfman et al. |
| 6,832,984 B2 | 12/2004 | Stelzer et al. |
| 6,835,193 B2 | 12/2004 | Epstein et al. |
| 6,837,867 B2 | 1/2005 | Kortelling |
| 6,863,672 B2 | 3/2005 | Reiley et al. |
| 6,869,430 B2 | 3/2005 | Balbierz et al. |
| 6,869,445 B1 | 3/2005 | Johnson |
| 6,875,219 B2 | 4/2005 | Arramon |
| 6,881,214 B2 | 4/2005 | Cosman et al. |
| 6,887,246 B2 | 5/2005 | Bhatnagar et al. |
| 6,899,715 B1 | 5/2005 | Beaty |
| 6,899,719 B2 | 5/2005 | Reiley et al. |
| 6,907,884 B2 | 6/2005 | Pellegrino et al. |
| 6,913,594 B2 | 7/2005 | Coleman et al. |
| 6,916,306 B1 | 7/2005 | Jenkins et al. |
| 6,923,813 B2 | 8/2005 | Phillips |
| 6,945,956 B2 | 9/2005 | Waldhauser et al. |
| 6,953,594 B2 | 10/2005 | Lee et al. |
| 6,955,716 B2 | 10/2005 | Xu et al. |
| 6,976,987 B2 | 12/2005 | Flores |
| 6,979,312 B2 | 12/2005 | Shimada |
| 6,979,352 B2 | 12/2005 | Reynolds |
| 6,981,981 B2 | 1/2006 | Reiley et al. |
| 6,991,616 B2 | 1/2006 | Bencini et al. |
| 6,998,128 B2 | 2/2006 | Haggard et al. |
| 7,004,930 B2 | 2/2006 | Marshall |
| 7,004,945 B2 | 3/2006 | Boyd et al. |
| 7,008,433 B2 | 3/2006 | Voellmicke et al. |
| 7,018,460 B2 | 3/2006 | Xu et al. |
| 7,022,133 B2 | 4/2006 | Yee et al. |
| 7,029,468 B2 | 4/2006 | Honebrink |
| 7,044,954 B2 | 5/2006 | Reiley et al. |
| 7,059,330 B1 | 6/2006 | Makower et al. |
| 7,063,682 B1 | 6/2006 | Whayne et al. |
| 7,066,942 B2 | 6/2006 | Treace |
| RE39,196 E | 7/2006 | Ying et al. |
| 7,081,122 B1 | 7/2006 | Reiley et al. |
| 7,081,161 B2 | 7/2006 | Genge et al. |
| 7,091,258 B2 | 8/2006 | Neubert et al. |
| 7,091,260 B2 | 8/2006 | Kühn |
| 7,094,202 B2 | 8/2006 | Nobis et al. |
| 7,094,286 B2 | 8/2006 | Liu |
| 7,108,696 B2 | 9/2006 | Daniel et al. |
| 7,109,254 B2 | 9/2006 | Müller et al. |
| 7,112,205 B2 | 9/2006 | Carrison |
| 7,114,501 B2 | 10/2006 | Johnson et al. |
| 7,138,442 B2 | 11/2006 | Smith et al. |
| 7,153,306 B2 | 12/2006 | Ralph et al. |

(56) References Cited

U.S. PATENT DOCUMENTS

| | | |
|---|---|---|
| 7,153,307 B2 | 12/2006 | Scribner et al. |
| 7,156,843 B2 | 1/2007 | Skarda |
| 7,156,845 B2 | 1/2007 | Mulier |
| 7,166,121 B2 | 1/2007 | Reiley et al. |
| 7,172,629 B2 | 2/2007 | McKay et al. |
| 7,179,255 B2 | 2/2007 | Lettice et al. |
| 7,186,234 B2 | 3/2007 | Dahla et al. |
| 7,186,761 B2 | 3/2007 | Soffiati et al. |
| 7,226,481 B2 | 6/2007 | Kuslich et al. |
| 7,252,671 B2 | 8/2007 | Scribner et al. |
| 7,160,296 B2 | 9/2007 | Pearson et al. |
| 7,267,683 B2 | 9/2007 | Sharkey et al. |
| 7,270,661 B2 | 9/2007 | Dahla et al. |
| 7,294,127 B2 | 11/2007 | Leung |
| 7,465,318 B2 | 12/2008 | Sennett et al. |
| 7,480,533 B2 | 1/2009 | Cosman et al. |
| 7,503,920 B2 | 3/2009 | Siegal |
| 7,544,196 B2 | 6/2009 | Bagga et al. |
| 7,559,932 B2 | 7/2009 | Truckai et al. |
| 7,569,054 B2 | 8/2009 | Michelson |
| 7,572,263 B2 | 8/2009 | Preissman |
| 7,591,822 B2 | 9/2009 | Olson, Jr. et al. |
| 7,595,634 B2 | 9/2009 | Flandre et al. |
| 7,625,364 B2 | 12/2009 | Corcoran et al. |
| 7,641,664 B2 | 1/2010 | Pagano |
| 7,731,720 B2 | 6/2010 | Sand et al. |
| 7,811,291 B2 | 10/2010 | Liu et al. |
| 7,824,403 B2 | 11/2010 | Vaska |
| 7,842,041 B2 | 11/2010 | Liu et al. |
| 7,887,543 B2 | 2/2011 | Sand et al. |
| 7,905,884 B2 | 3/2011 | Simonton et al. |
| 7,918,874 B2 | 4/2011 | Siegal |
| 7,972,340 B2 | 7/2011 | Sand et al. |
| 7,976,542 B1 | 7/2011 | Cosman |
| 8,034,071 B2 | 10/2011 | Scribner et al. |
| 8,246,627 B2 | 8/2012 | Vanleeuwen et al. |
| 8,284,128 B2 | 10/2012 | Kimura |
| 8,518,036 B2 | 8/2013 | Leung |
| 8,583,260 B2 | 11/2013 | Knudson |
| 8,591,507 B2 | 11/2013 | Kramer et al. |
| 8,663,226 B2 | 3/2014 | Germain |
| RE44,883 E | 5/2014 | Cha |
| 8,758,349 B2 | 6/2014 | Germain et al. |
| 8,827,981 B2 | 9/2014 | Liu et al. |
| 8,864,760 B2 | 10/2014 | Kramer et al. |
| 8,936,631 B2 | 1/2015 | Nguyen |
| 9,113,974 B2 | 8/2015 | Germain |
| 9,125,671 B2 | 9/2015 | Germain et al. |
| 9,161,809 B2 | 10/2015 | Germain et al. |
| 9,421,057 B2 | 8/2016 | Germain |
| 9,743,938 B2 | 8/2017 | Germain et al. |
| 2001/0011174 A1 | 8/2001 | Reiley et al. |
| 2001/0023349 A1 | 9/2001 | Van Tassel et al. |
| 2002/0007180 A1 | 1/2002 | Wittenberger et al. |
| 2002/0013600 A1 | 1/2002 | Scribner et al. |
| 2002/0026195 A1 | 2/2002 | Layne et al. |
| 2002/0026197 A1 | 2/2002 | Foley et al. |
| 2002/0068929 A1 | 6/2002 | Zvuloni |
| 2002/0068974 A1 | 6/2002 | Kuslich et al. |
| 2002/0077595 A1 | 6/2002 | Hundertmark et al. |
| 2002/0082605 A1 | 6/2002 | Reiley et al. |
| 2002/0115742 A1 | 8/2002 | Trieu et al. |
| 2002/0128638 A1 | 9/2002 | Chauvel et al. |
| 2002/0133148 A1 | 9/2002 | Daniel et al. |
| 2002/0156483 A1 | 10/2002 | Voellmicke et al. |
| 2002/0188299 A1 | 12/2002 | Reiley et al. |
| 2002/0188300 A1 | 12/2002 | Arramon et al. |
| 2003/0014094 A1 | 1/2003 | Hammack et al. |
| 2003/0032929 A1 | 2/2003 | McGuckin |
| 2003/0036763 A1 | 2/2003 | Bhatnagar et al. |
| 2003/0043963 A1 | 3/2003 | Yamagami et al. |
| 2003/0050644 A1 | 3/2003 | Boucher et al. |
| 2003/0069522 A1 | 4/2003 | Jasobsen et al. |
| 2003/0073979 A1 | 4/2003 | Naimark et al. |
| 2003/0130664 A1 | 7/2003 | Boucher et al. |
| 2003/0163085 A1 | 8/2003 | Tanner et al. |
| 2003/0171744 A1 | 9/2003 | Leung et al. |
| 2003/0191489 A1 | 10/2003 | Reiley et al. |
| 2003/0195547 A1 | 10/2003 | Scribner et al. |
| 2003/0212394 A1 | 11/2003 | Pearson et al. |
| 2003/0212395 A1 | 11/2003 | Woloszko et al. |
| 2003/0220414 A1 | 11/2003 | Axen et al. |
| 2003/0225432 A1 | 12/2003 | Baptiste et al. |
| 2003/0233096 A1 | 12/2003 | Osorio et al. |
| 2004/0023384 A1 | 2/2004 | Fukaya |
| 2004/0023784 A1 | 2/2004 | Yu et al. |
| 2004/0024081 A1 | 2/2004 | Trieu et al. |
| 2004/0024398 A1 | 2/2004 | Hovda et al. |
| 2004/0024409 A1 | 2/2004 | Sand et al. |
| 2004/0024410 A1 | 2/2004 | Olson et al. |
| 2004/0034384 A1 | 2/2004 | Fukaya |
| 2004/0044096 A1 | 3/2004 | Smith et al. |
| 2004/0044350 A1 | 3/2004 | Martin et al. |
| 2004/0059328 A1 | 3/2004 | Daniel et al. |
| 2004/0087936 A1 | 5/2004 | Stern et al. |
| 2004/0087994 A1 | 5/2004 | Suddaby |
| 2004/0092946 A1 | 5/2004 | Bagga et al. |
| 2004/0097612 A1 | 5/2004 | Rosenberg et al. |
| 2004/0111136 A1 | 6/2004 | Sharkey et al. |
| 2004/0127987 A1 | 7/2004 | Evans et al. |
| 2004/0133208 A1 | 7/2004 | Weikel et al. |
| 2004/0138758 A1 | 7/2004 | Evans et al. |
| 2004/0153064 A1 | 8/2004 | Foley et al. |
| 2004/0153115 A1 | 8/2004 | Reiley et al. |
| 2004/0158237 A1 | 8/2004 | Abboud et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0210231 A1 | 10/2004 | Broucher et al. |
| 2004/0215343 A1 | 10/2004 | Hochschuler et al. |
| 2004/0220577 A1 | 11/2004 | Cragg |
| 2004/0220680 A1 | 11/2004 | Yamamoto et al. |
| 2004/0225296 A1 | 11/2004 | Reiss et al. |
| 2004/0226479 A1 | 11/2004 | Lyles et al. |
| 2004/0230309 A1 | 11/2004 | DiMauro et al. |
| 2004/0236186 A1 | 11/2004 | Chu |
| 2004/0247644 A1 | 12/2004 | Bratt et al. |
| 2004/0267271 A9 | 12/2004 | Scribner et al. |
| 2005/0027245 A1 | 2/2005 | Sachdeva et al. |
| 2005/0033303 A1 | 2/2005 | Chappuis et al. |
| 2005/0038383 A1 | 2/2005 | Kelley et al. |
| 2005/0038422 A1 | 2/2005 | Maurice |
| 2005/0043737 A1 | 2/2005 | Reiley et al. |
| 2005/0055030 A1 | 3/2005 | Falahee |
| 2005/0060030 A1 | 3/2005 | Lashinski et al. |
| 2005/0070844 A1 | 3/2005 | Chow et al. |
| 2005/0070912 A1 | 3/2005 | Voellmicke |
| 2005/0070915 A1 | 3/2005 | Mazzuca et al. |
| 2005/0090852 A1 | 4/2005 | Layne et al. |
| 2005/0113636 A1 | 5/2005 | Lozier et al. |
| 2005/0119650 A1 | 6/2005 | Sanders et al. |
| 2005/0124989 A1 | 6/2005 | Suddaby |
| 2005/0143827 A1 | 6/2005 | Globerman et al. |
| 2005/0177168 A1 | 8/2005 | Brunnett et al. |
| 2005/0177210 A1 | 8/2005 | Lueng et al. |
| 2005/0182413 A1 | 8/2005 | Johnson et al. |
| 2005/0187556 A1 | 8/2005 | Stack et al. |
| 2005/0199156 A1 | 9/2005 | Khairoun et al. |
| 2005/0209557 A1 | 9/2005 | Carroll et al. |
| 2005/0216018 A1 | 9/2005 | Sennett |
| 2005/0228391 A1 | 10/2005 | Levy et al. |
| 2005/0234425 A1 | 10/2005 | Miller et al. |
| 2005/0240193 A1 | 10/2005 | Layne et al. |
| 2005/0251266 A1 | 11/2005 | Maspero et al. |
| 2005/0251267 A1 | 11/2005 | Winterbottom et al. |
| 2005/0261683 A1 | 11/2005 | Veldhuizen et al. |
| 2005/0283148 A1 | 12/2005 | Janssen |
| 2005/0287771 A1 | 12/2005 | Seamons et al. |
| 2006/0024348 A1 | 2/2006 | Engqvist et al. |
| 2006/0025763 A1 | 2/2006 | Nelson et al. |
| 2006/0041033 A1 | 2/2006 | Bisig et al. |
| 2006/0052743 A1 | 3/2006 | Reynolds |
| 2006/0064101 A1 | 3/2006 | Arramon |
| 2006/0074433 A1 | 4/2006 | McGill et al. |

(56) References Cited

U.S. PATENT DOCUMENTS

| | | |
|---|---|---|
| 2006/0084977 A1 | 4/2006 | Lieberman |
| 2006/0085009 A1 | 4/2006 | Truckai et al. |
| 2006/0100635 A1 | 5/2006 | Reiley et al. |
| 2006/0100706 A1 | 5/2006 | Shadduck et al. |
| 2006/0106392 A1 | 5/2006 | Embry |
| 2006/0106459 A1 | 5/2006 | Truckai et al. |
| 2006/0116689 A1 | 6/2006 | Albans et al. |
| 2006/0116690 A1 | 6/2006 | Pagano |
| 2006/0122623 A1 | 6/2006 | Truckai et al. |
| 2006/0142732 A1 | 6/2006 | Karmarkar et al. |
| 2006/0149268 A1 | 7/2006 | Truckai et al. |
| 2006/0149281 A1 | 7/2006 | Reiley et al. |
| 2006/0156959 A1 | 7/2006 | Engqvist et al. |
| 2006/0184106 A1 | 8/2006 | McDaniel et al. |
| 2006/0184192 A1 | 8/2006 | Markworth et al. |
| 2006/0200121 A1 | 9/2006 | Mowery |
| 2006/0206116 A1 | 9/2006 | Yeung |
| 2006/0206136 A1 | 9/2006 | Sachdeva et al. |
| 2006/0217704 A1 | 9/2006 | Cockburn et al. |
| 2006/0217736 A1 | 9/2006 | Kaneko |
| 2006/0229625 A1 | 10/2006 | Truckai et al. |
| 2006/0229631 A1 | 10/2006 | Reiley et al. |
| 2006/0235417 A1 | 10/2006 | Sala |
| 2006/0259023 A1 | 11/2006 | Abboud et al. |
| 2006/0264819 A1 | 11/2006 | Fischer et al. |
| 2006/0264945 A1 | 11/2006 | Edidin et al. |
| 2006/0266372 A1 | 11/2006 | Miller et al. |
| 2006/0270750 A1 | 11/2006 | Almen et al. |
| 2006/0271061 A1 | 11/2006 | Beyar et al. |
| 2006/0276797 A1 | 12/2006 | Botimer |
| 2006/0276819 A1 | 12/2006 | Osorio et al. |
| 2006/0293687 A1 | 12/2006 | Bogert |
| 2007/0006692 A1 | 1/2007 | Phan |
| 2007/0010845 A1 | 1/2007 | Gong et al. |
| 2007/0016130 A1 | 1/2007 | Leeflang et al. |
| 2007/0016211 A1 | 1/2007 | Botimer |
| 2007/0021769 A1 | 1/2007 | Scribner et al. |
| 2007/0043373 A1 | 2/2007 | Sala |
| 2007/0055201 A1 | 3/2007 | Seto et al. |
| 2007/0055260 A1 | 3/2007 | Cragg |
| 2007/0055266 A1 | 3/2007 | Osorio et al. |
| 2007/0055275 A1 | 3/2007 | Schaller |
| 2007/0055277 A1 | 3/2007 | Osorio et al. |
| 2007/0055278 A1 | 3/2007 | Osorio et al. |
| 2007/0055279 A1 | 3/2007 | Sand et al. |
| 2007/0055281 A1 | 3/2007 | Osorio et al. |
| 2007/0055283 A1 | 3/2007 | Scribner |
| 2007/0055284 A1 | 3/2007 | Osorio |
| 2007/0055285 A1 | 3/2007 | Osorio et al. |
| 2007/0055300 A1 | 3/2007 | Osorio et al. |
| 2007/0055382 A1 | 3/2007 | Osorio et al. |
| 2007/0059281 A1 | 3/2007 | Moseley et al. |
| 2007/0067034 A1 | 3/2007 | Chirico et al. |
| 2007/0093840 A1 | 4/2007 | Pacelli |
| 2007/0114248 A1 | 5/2007 | Kovac |
| 2007/0118142 A1 | 5/2007 | Krueger et al. |
| 2007/0118143 A1 | 5/2007 | Ralph et al. |
| 2007/0142642 A1 | 6/2007 | Krueger et al. |
| 2007/0156130 A1 | 7/2007 | Thistle |
| 2007/0162042 A1 | 7/2007 | Dunker |
| 2007/0173939 A1 | 7/2007 | Kim et al. |
| 2007/0185231 A1 | 8/2007 | Liu et al. |
| 2007/0197935 A1 | 8/2007 | Reiley |
| 2007/0198023 A1 | 8/2007 | Sand et al. |
| 2007/0203500 A1* | 8/2007 | Gordon .............. A61B 17/1617 606/96 |
| 2007/0211563 A1 | 9/2007 | DeVries |
| 2007/0233146 A1 | 10/2007 | Henniges et al. |
| 2007/0260223 A1 | 11/2007 | Scheibe et al. |
| 2007/0260257 A1 | 11/2007 | Phan |
| 2007/0270876 A1 | 11/2007 | Kuo et al. |
| 2007/0276319 A1 | 11/2007 | Betts |
| 2007/0282305 A1 | 12/2007 | Goldfarb et al. |
| 2008/0004615 A1 | 1/2008 | Woloszko et al. |
| 2008/0033422 A1 | 2/2008 | Turner et al. |
| 2008/0058725 A1 | 3/2008 | Scribner et al. |
| 2008/0058821 A1 | 3/2008 | Maurer et al. |
| 2008/0058827 A1 | 3/2008 | Osorio et al. |
| 2008/0058840 A1 | 3/2008 | Albrecht |
| 2008/0065020 A1 | 3/2008 | Ralph et al. |
| 2008/0065087 A1 | 3/2008 | Osorio et al. |
| 2008/0065190 A1 | 3/2008 | Osorio et al. |
| 2008/0086142 A1 | 4/2008 | Kohm et al. |
| 2008/0140079 A1 | 6/2008 | Osorio et al. |
| 2008/0183165 A1 | 7/2008 | Buysee et al. |
| 2008/0183265 A1 | 7/2008 | Bly |
| 2008/0195112 A1 | 8/2008 | Liu et al. |
| 2008/0208255 A1 | 8/2008 | Siegal |
| 2008/0221608 A1 | 9/2008 | Betts |
| 2008/0228192 A1 | 9/2008 | Beyer et al. |
| 2008/0249481 A1 | 10/2008 | Crainich |
| 2008/0249525 A1 | 10/2008 | Lee et al. |
| 2008/0255571 A1 | 10/2008 | Truckai et al. |
| 2008/0269766 A1 | 10/2008 | Justis |
| 2008/0269796 A1 | 10/2008 | Reiley et al. |
| 2008/0287741 A1 | 11/2008 | Ostrovsky et al. |
| 2008/0294167 A1 | 11/2008 | Schumacher et al. |
| 2009/0076517 A1 | 3/2009 | Reiley et al. |
| 2009/0105775 A1 | 4/2009 | Mitchell et al. |
| 2009/0131867 A1 | 5/2009 | Liu et al. |
| 2009/0131886 A1 | 5/2009 | Liu et al. |
| 2009/0131945 A1 | 5/2009 | Liu et al. |
| 2009/0131948 A1 | 5/2009 | Liu |
| 2009/0131950 A1 | 5/2009 | Liu et al. |
| 2009/0131986 A1 | 5/2009 | Lee |
| 2009/0182427 A1 | 7/2009 | Liu et al. |
| 2009/0198243 A1 | 8/2009 | Melsheimer |
| 2009/0264862 A1 | 10/2009 | Neidert et al. |
| 2009/0264892 A1 | 10/2009 | Beyar et al. |
| 2009/0292289 A9 | 11/2009 | Sand et al. |
| 2009/0293687 A1 | 12/2009 | Nino et al. |
| 2009/0299282 A1 | 12/2009 | Lau et al. |
| 2010/0057087 A1 | 3/2010 | Cha |
| 2010/0082033 A1 | 4/2010 | Germain |
| 2010/0114184 A1 | 5/2010 | Degtyar |
| 2010/0121332 A1 | 5/2010 | Crainich et al. |
| 2010/0152724 A1 | 6/2010 | Marion et al. |
| 2010/0160922 A1 | 6/2010 | Liu et al. |
| 2010/0211076 A1 | 8/2010 | Germain et al. |
| 2010/0274270 A1 | 10/2010 | Patel |
| 2010/0298832 A1 | 11/2010 | Lau et al. |
| 2011/0034884 A9 | 2/2011 | Pellegrino et al. |
| 2011/0098701 A1 | 4/2011 | McIntyre et al. |
| 2011/0160737 A1 | 6/2011 | Steffen et al. |
| 2011/0251615 A1 | 10/2011 | Truckai et al. |
| 2011/0295261 A1 | 12/2011 | Germain |
| 2011/0295262 A1 | 12/2011 | Germain et al. |
| 2011/0301590 A1 | 12/2011 | Podhajsky et al. |
| 2012/0065543 A1 | 3/2012 | Ireland |
| 2012/0130381 A1 | 5/2012 | Germain |
| 2012/0158004 A1 | 6/2012 | Burger et al. |
| 2012/0191095 A1 | 7/2012 | Burger et al. |
| 2012/0239049 A1 | 9/2012 | Truckai |
| 2012/0265186 A1 | 10/2012 | Burger et al. |
| 2012/0277730 A1 | 11/2012 | Salahieh |
| 2012/0330180 A1 | 12/2012 | Pellegrino et al. |
| 2012/0330301 A1 | 12/2012 | Pellegrino et al. |
| 2013/0006232 A1 | 1/2013 | Pellegrino |
| 2013/0041377 A1 | 2/2013 | Kuntz |
| 2013/0072941 A1 | 3/2013 | Tan-Malecki et al. |
| 2013/0231654 A1 | 9/2013 | Germain |
| 2013/0237795 A1 | 9/2013 | Carr |
| 2013/0261615 A1 | 10/2013 | Kramer et al. |
| 2013/0261621 A1 | 10/2013 | Kramer et al. |
| 2013/0345709 A1 | 12/2013 | Burger et al. |
| 2014/0135779 A1 | 5/2014 | Germain |
| 2014/0163566 A1 | 6/2014 | Phan et al. |
| 2014/0316413 A1 | 10/2014 | Burger et al. |
| 2014/0350542 A1 | 11/2014 | Kramer et al. |
| 2014/0371740 A1 | 12/2014 | Germain et al. |
| 2015/0216594 A1 | 8/2015 | Prakash |
| 2015/0265333 A1 | 9/2015 | Shin et al. |
| 2015/0297246 A1* | 10/2015 | Patel .................. A61B 17/1671 606/79 |

(56) References Cited

U.S. PATENT DOCUMENTS

| | | | |
|---|---|---|---|
| 2015/0313614 | A1 | 11/2015 | Germain |
| 2016/0066984 | A1 | 3/2016 | Janssen et al. |
| 2016/0228131 | A1 | 8/2016 | Brockman et al. |
| 2017/0095291 | A1 | 4/2017 | Harrington |
| 2017/0105798 | A1 | 4/2017 | Allison |
| 2018/0078170 | A1 | 3/2018 | Panescu et al. |
| 2018/0147006 | A1 | 5/2018 | Purdy |
| 2018/0147007 | A1 | 5/2018 | Purdy |
| 2020/0078066 | A1 | 3/2020 | Purdy et al. |

FOREIGN PATENT DOCUMENTS

| | | |
|---|---|---|
| CN | 2841051 | 11/2006 |
| EP | 1459691 | 9/2004 |
| JP | 2004242936 | 9/2004 |
| JP | 2008510530 | 4/2008 |
| JP | 2008528081 | 7/2008 |
| JP | 2008541878 | 11/2008 |
| JP | 2010063887 | 3/2010 |
| JP | 2011500156 | 1/2011 |
| WO | 1993004634 | 3/1993 |
| WO | 1996013297 | 5/1996 |
| WO | 1996020752 | 7/1996 |
| WO | 1997003611 | 2/1997 |
| WO | 2002003870 | 1/2002 |
| WO | 2003101308 | 12/2003 |
| WO | 2005122938 | 12/2005 |
| WO | 2007036815 | 4/2007 |
| WO | 2007087400 | 8/2007 |
| WO | 2008076330 | 6/2008 |
| WO | 2008084479 | 7/2008 |
| WO | 2010039894 | 4/2010 |
| WO | 2010081187 | 7/2010 |
| WO | 2010135602 | 11/2010 |
| WO | 2010135606 | 11/2010 |
| WO | 2011066465 | 6/2011 |
| WO | 2011114602 | 9/2011 |
| WO | 2011137357 | 11/2011 |
| WO | 2011137377 | 11/2011 |
| WO | 2012071464 | 5/2012 |
| WO | 2013147990 | 10/2013 |
| WO | 2014093673 | 6/2014 |

OTHER PUBLICATIONS

Park, et al., Biomaterials: An Introduction—Second Edition, Plenum Press ,1992 ,177-178.
Park, et al., The Materials Properties of Bone-Particle Impregnated PMMA, Journal of Biomedical Engineering, vol. 108 ,1986 ,141-148.
Office Action dated Dec. 9, 2009 for U.S. Appl. No. 12/262,064.
Office Action dated Dec. 11, 2009 for U.S. Appl. No. 12/261,987.
Disc-O-Tech confidence Cement System at http://www.disc-o-tech.com/Articles/Article.asp?CategoryID=4&ArticleID=168 accessed, ,Dec. 3, 2007.
Dai, et al., Bone-Particle-Impregnated Bone Cement: an in vivo weight-bearing study, Journal Biomedical Materials Search, vol. 25 ,191 ,141-156.
Hasenwinkel, et al.,"A Novel High-Viscosity, Two-Solution Acrylic Bone Cement: Effect of Chemical Composition on Properties", J. Biomed Mater. Res. vol. 47, No. 1 ,1999 ,36-45.
Klawitter, et al., Application of Porous Ceramics for the Attachment of Load Bearing Internal Orthopedic Applications, J. Biomed. Mater. Res. Symp., 2(1) ,1972 ,61-229.
Liu, et al., Bone-Particle-Impregnanted Bone Cement: An In Vitro Study, Journal of Biomedical Materials Research, vol. 21 ,1987 ,247-261.
Office Action dated Dec. 2, 2009 for U.S. Appl. No. 12/029,428.
Office Action dated Nov. 5, 2008 for U.S. Appl. No. 11/941,733.
European Examination Report dated Dec. 19, 2017 for EP13767383.6.
European Search Report dated Jan. 7, 2019 for EP16793433.0.
European Search Report dated Jun. 8, 2017 for EP17154660.9.
International Search Report and Written Opinion dated Jan. 9, 2012 for PCT/US2011/034185.
International Search Report and Written Opinion dated Jan. 22, 2009 for PCT/US2008/83698.
International Search Report and Written Opinion dated Feb. 7, 2018 for PCT/US2017/058303.
International Search Report and Written Opinion dated Feb. 21, 2018 for PCT/US2017/063281.
International Search Report and Written Opinion dated Mar. 30, 2018 for PCT/US2017/065328.
International Search Report and Written Opinion dated Jul. 20, 2010 for PCT/US2010/035687.
International Search Report and Written Opinion dated Jul. 26, 2011 for PCT/US2011/034628.
International Search Report and Written Opinion dated Aug. 25, 2009 for PCT/US2009/035726.
Notice of Allowance dated Jan. 4, 2017 for U.S. Appl. No. 13/302,927.
Notice of Allowance dated Feb. 21, 2019 for U.S. Appl. No. 14/139,372.
Notice of Allowance dated Apr. 3, 2019 for U.S. Appl. No. 15/349,715.
Notice of Allowance dated May 3, 2017 for U.S. Appl. No. 14/815,620.
Notice of Allowance dated May 11, 2018 for U.S. Appl. No. 14/453,427.
Notice of Allowance dated May 26, 2015 for U.S. Appl. No. 13/098,116.
Notice of Allowance dated Nov. 9, 2017 for U.S. Appl. No. 14/815,812.
Office Action dated Jan. 18, 2017 for U.S. Appl. No. 14/815,620.
Office Action dated Jan. 26, 2011 for U.S. Appl. No. 11/941,764.
Office Action dated Jan. 26, 2017 for U.S. Appl. No. 14/815,812.
Office Action dated Feb. 23, 2010 for U.S. Appl. No. 11/941,733.
Office Action dated Feb. 23, 2010 for U.S. Appl. No. 11/941,764.
Office Action dated dated Mar. 21, 2011 for U.S. Appl. No. 11/941,764.
Office Action dated Mar. 21, 2011 for U.S. Appl. No. 12/029,428.
Office Action dated Apr. 24, 2017 for U.S. Appl. No. 14/453,427.
Office Action dated Apr. 26, 2010 for U.S. Appl. No. 12/029,428.
Office Action dated May 1, 2009 for U.S. Appl. No. 12/261,987.
Office Action dated May 5, 2010 for U.S. Appl. No. 11/941,764.
Office Action dated May 6, 2019 for U.S. Appl. No. 15/675,315.
Office Action dated May 13, 2009 for U.S. Appl. No. 12/029,428.
Office Action dated May 17, 2010 for U.S. Appl. No. 12/261,987.
Office Action dated May 21, 2014 for U.S. Appl. No. 13/098,116.
Office Action dated May 31, 2016 for U.S. Appl. No. 14/815,620.
Office Action dated Jun. 8, 2009 for U.S. Appl. No. 11/941,764.
Office Action dated Jun. 12, 2009 for U.S. Appl. No. 11/941,733.
Office Action dated Jun. 21, 2013 for U.S. Appl. No. 13/215,098.
Office Action dated Jul. 11, 2017 for U.S. Appl. No. 14/815,812.
Office Action dated Jul. 12, 2010 for U.S. Appl. No. 11/941,764.
Office Action dated Jul. 25, 2011 for U.S. Appl. No. 11/941,733.
Office Action dated Jul. 29, 2013 for U.S. Appl. No. 13/098,116.
Office Action dated Sep. 1, 2010 for U.S. Appl. No. 12/029,428.
Office Action dated Oct. 2, 2018 for U.S. Appl. No. 14/139,372.
Office Action dated Oct. 30, 2018 for U.S. Appl. No. 15/349,715.
Office Action dated Nov. 3, 2008 for U.S. Appl. No. 11/941,764.
Office Action dated Nov. 3, 2008 for U.S. Appl. No. 12/029,428.
Notice of Allowance dated Dec. 13, 2018 for U.S. Appl. No. 15/917,454.
European Search Report dated Nov. 15, 2017 for EP09818476.5.
Search Report dated Nov. 16, 2016 for EP14772615.2.
International Search Report and Written Opinion dated Nov. 20, 2009 for PCT/US2009/059113.
Allowance dated Jan. 18, 2017 for U.S. Appl. No. 13/097,998.
Allowance dated Apr. 9, 2014 for U.S. Appl. No. 12/578,455.
Allowance dated Apr. 23, 2018 for U.S. Appl. No. 13/083,411.
Allowance dated Aug. 24, 2018 for U.S. Appl. No. 15/388,598.
Allowance dated Oct. 28, 2016 for U.S. Appl. No. 13/853,397.
Allowance dated Nov. 8, 2013 for U.S. Appl. No. 12/578,455.
Allowance dated Nov. 18, 2016 for U.S. Appl. No. 13/097,998.
Allowance dated Nov. 25, 2013 for U.S. Appl. No. 12/571,174.

(56) References Cited

OTHER PUBLICATIONS

Allowance dated Nov. 25, 2016 for U.S. Appl. No. 13/853,397.
Notice of Allowance dated Dec. 28, 2017 for U.S. Appl. No. 15/211,359.
Notice of Allowance dated Aug. 31, 2016 for U.S. Appl. No. 14/887,007.
Office Action dated Feb. 3, 2016 for U.S. Appl. No. 13/853,397.
Office Action dated Feb. 10, 2015 for U.S. Appl. No. 13/083,411.
Office Action dated Mar. 1, 2017 for U.S. Appl. No. 15/211,359.
Office Action dated Apr. 19, 2018 for U.S. Appl. No. 15/388,598.
Office Action dated May 24, 2012 for U.S. Appl. No. 12/578,455.
Office Action dated Jun. 4, 2018 for U.S. Appl. No. 15/349,715.
Office Action dated Jun. 22, 2018 for U.S. Appl. No. 15/917,454.
Office Action dated Jun. 25, 2015 for U.S. Appl. No. 13/853,397.
Office Action dated Jun. 29, 2018 for U.S. Appl. No. 15/449,591.
Office Action dated Jul. 12, 2017 for U.S. Appl. No. 13/083,411.
Office Action dated Jul. 30, 2013 for U.S. Appl. No. 13/083,411.
Office Action dated Sep. 6, 2017 for U.S. Appl. No. 15/211,359.
Office Action dated Sep. 26, 2017 for U.S. Appl. No. 15/388,598.
Office Action dated Nov. 12, 2013 for U.S. Appl. No. 13/083,411.
Office Action dated Nov. 25, 2016 for U.S. Appl. No. 13/083,411.
Office Action dated Dec. 3, 2012 for U.S. Appl. No. 12/571,174.
Office Action dated Feb. 27, 2013 for U.S. Appl. No. 12/578,455.
Office Action dated Jul. 12, 2016 for U.S. Appl. No. 14/887,007.
Office Action dated Sep. 10, 2013 for U.S. Appl. No. 12/571,174.
Notice of Allowance dated Aug. 8, 2019 for U.S. Appl. No. 15/836,125.
Notice of Allowance dated Aug. 9, 2019 for U.S. Appl. No. 15/836,241.
International Search Report and Written Opinion dated Apr. 23, 2016 for PCT/US2018/012372.
Office Action dated Dec. 26, 2019 for U.S. Appl. No. 15/822,864.
Notice of Allowance dated Sep. 20, 2019 for U.S. Appl. No. 15/793,509.
Office Action dated Nov. 7, 2019 for U.S. Appl. No. 15/675,315.
Notice of Allowance dated Feb. 19, 2020 for U.S. Appl. No. 15/675,315.
International Search Report and Written Opinion dated Apr. 8, 2020 for PCT/US2019060279.

* cited by examiner

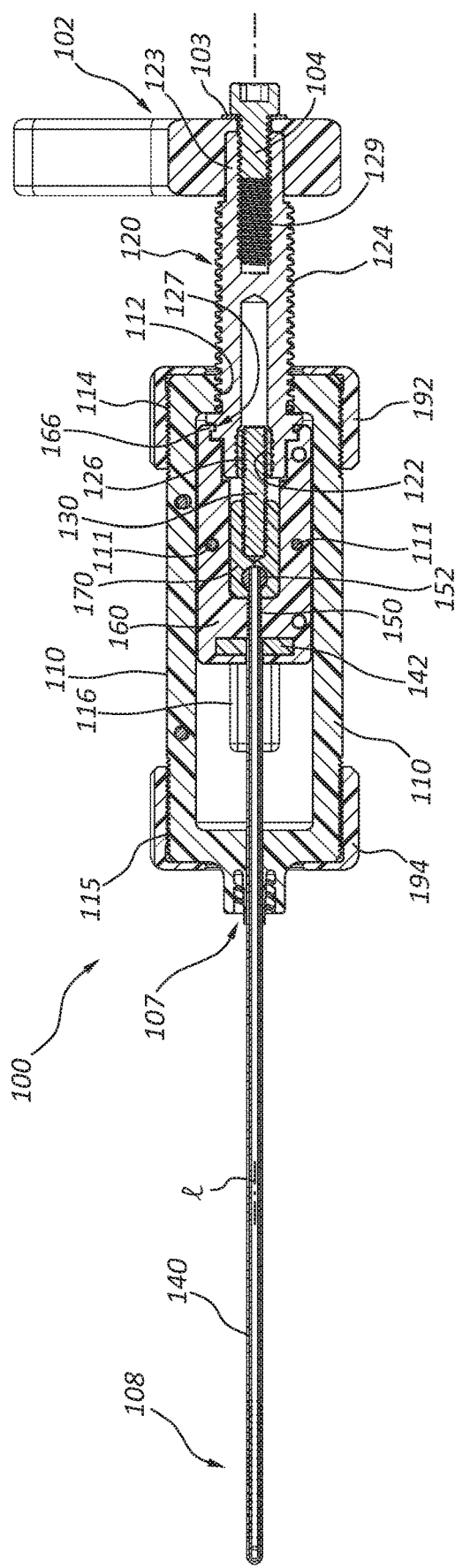
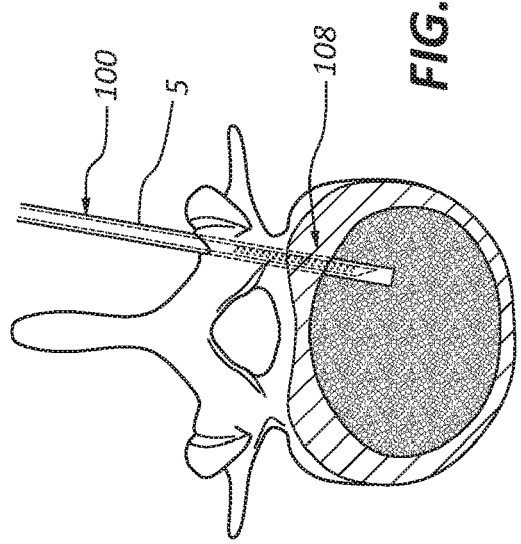
FIG. 10A
FIG. 10B

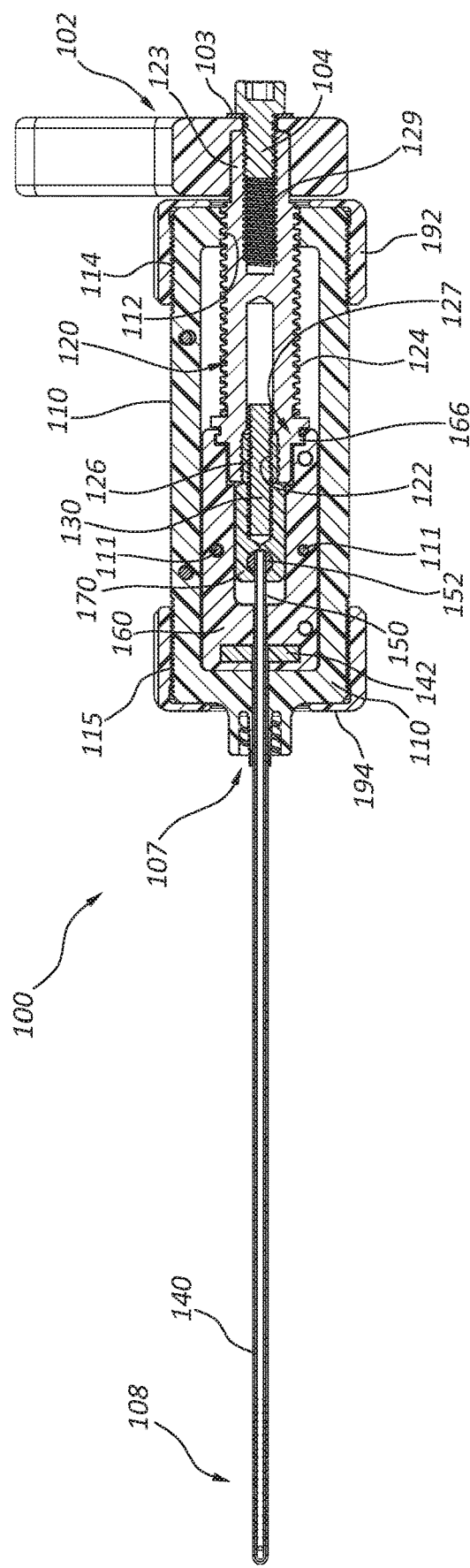
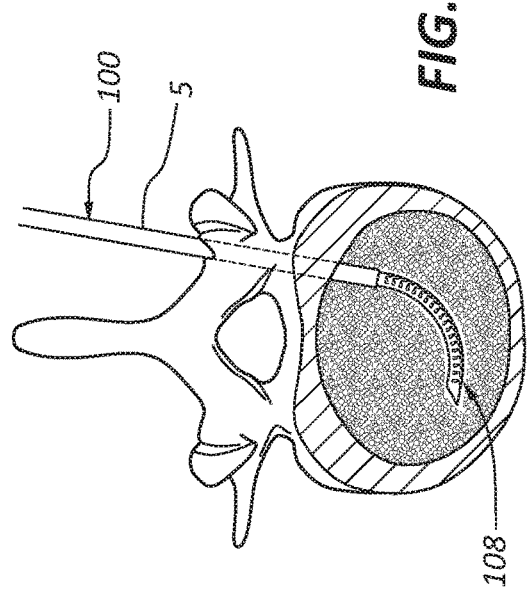
FIG. 12A
FIG. 12B

OSTEOTOME WITH A DISTAL PORTION FOR SIMULTANEOUS ADVANCEMENT AND ARTICULATION

RELATED APPLICATIONS

This application claims priority to U.S. Provisional Application No. 62/443,371, filed on Jan. 6, 2017 and titled, "Osteotome with a Distal Portion For Simultaneous Advancement and Articulation," which is hereby incorporated by reference in its entirety.

TECHNICAL FIELD

The present disclosure relates generally to the field of medical devices. More particularly, some embodiments relate to osteotomes that are configured for simultaneous advancement and articulation of a distal portion of the osteotome. Related methods and systems are also disclosed.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 10A is a cross-sectional view of the osteotome of FIG. 1 in a first configuration.

FIG. 10B depicts the osteotome of FIG. 1 in a vertebra of the patient when the osteotome is in the first configuration.

FIG. 12A is a cross-sectional view of the osteotome of FIG. 1 in a third configuration.

FIG. 12B depicts the osteotome of FIG. 1 in a vertebra of the patient when the osteotome is in the third configuration.

DETAILED DESCRIPTION

Figure 1:
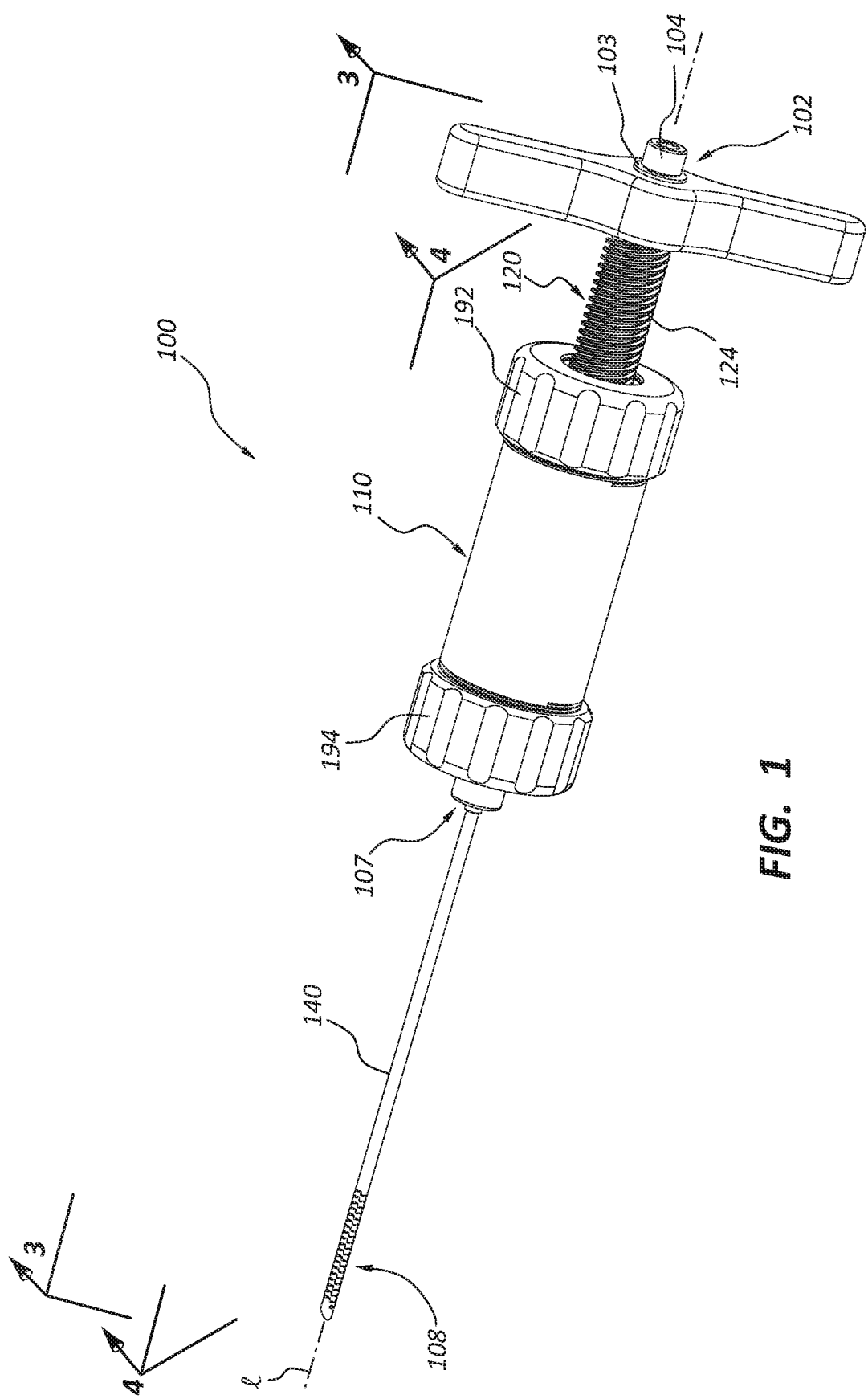
FIG. 1 is a perspective view of an osteotome.

An osteotome may be used to create or expand a cavity within bone of a patient. For example, in some embodiments, a distal portion of an osteotome may be inserted into a bone (e.g., a vertebra) of the patient. Once the distal portion of the osteotome is disposed within the bone of the patient, the distal portion of the osteotome may be displaced. Such displacement may cut, grind, granulate, fragmentize, deform, displace, or otherwise alter the bone, thereby creating and/or expanding a cavity within the bone.

As the distal portion of the osteotome is displaced, the bone of the patient may exert one or more forces on the distal portion of the osteotome. For example, in some embodiments where the distal portion of the osteotome is transitioned from a linear configuration to a bent configuration without simultaneous advancement of the distal portion of the osteotome in a distal direction, the distal portion of the osteotome may contact bone that exerts one or more reactionary forces on the distal portion. Such force(s) may damage or weaken the osteotome.

In some embodiments described herein, the osteotome may be manipulated such that a distal portion of the osteotome is simultaneously advanced and articulated. For example, in some embodiments, rotation of a handle may cause the distal portion of the osteotome to simultaneously both (1) be advanced within the bone of the patient and (2) bend away from a longitudinal axis of the osteotome. Relative to other methods, the simultaneous advancement and articulation of a distal portion of an osteotome may reduce the magnitude of one or more forces that may act on the distal portion of the osteotome. Stated differently, simultaneous advancement and articulation of the distal portion may reduce one or more forces on the distal portion of the osteotome relative to other methods in which advancement and articulation are separated in time, thereby decreasing the risk of breakage or other damage to the osteotome.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Two components may be coupled to each other even though they are not in direct contact with each other. For example, two components may be coupled to each other through an intermediate component. Two components are "fixedly coupled" to each other if neither component is displaceable relative to the other. The phrase "attached to" refers to interaction between two or more entities which are in direct contact with each other and/or are separated from each other only by a fastener of any suitable variety (e.g., an adhesive).

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Figure 2:
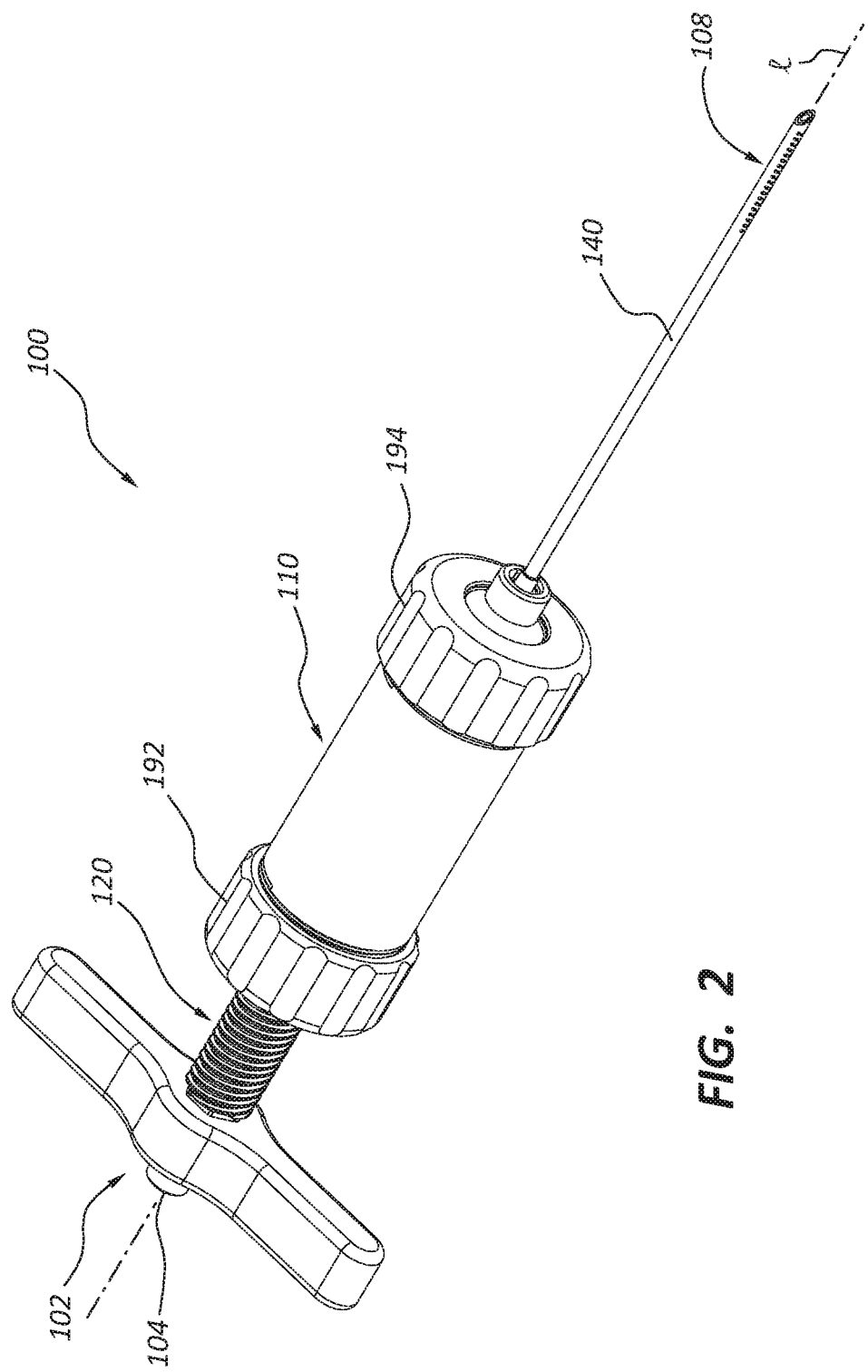
FIG. 2 is an alternative perspective view of the osteotome of FIG. 1.
Figure 3:
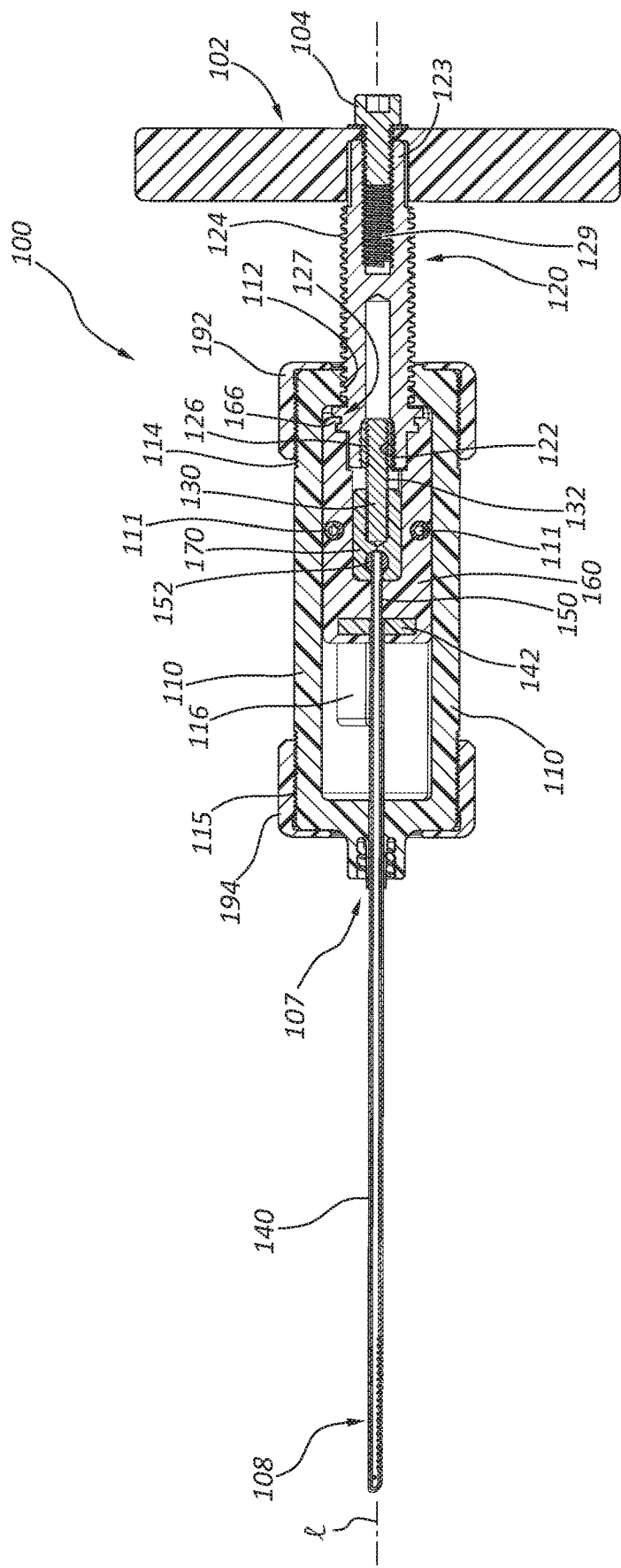
FIG. 3 is a cross-sectional view of the osteotome of FIG. 1 through plane 3-3 of FIG. 1.
Figure 4:
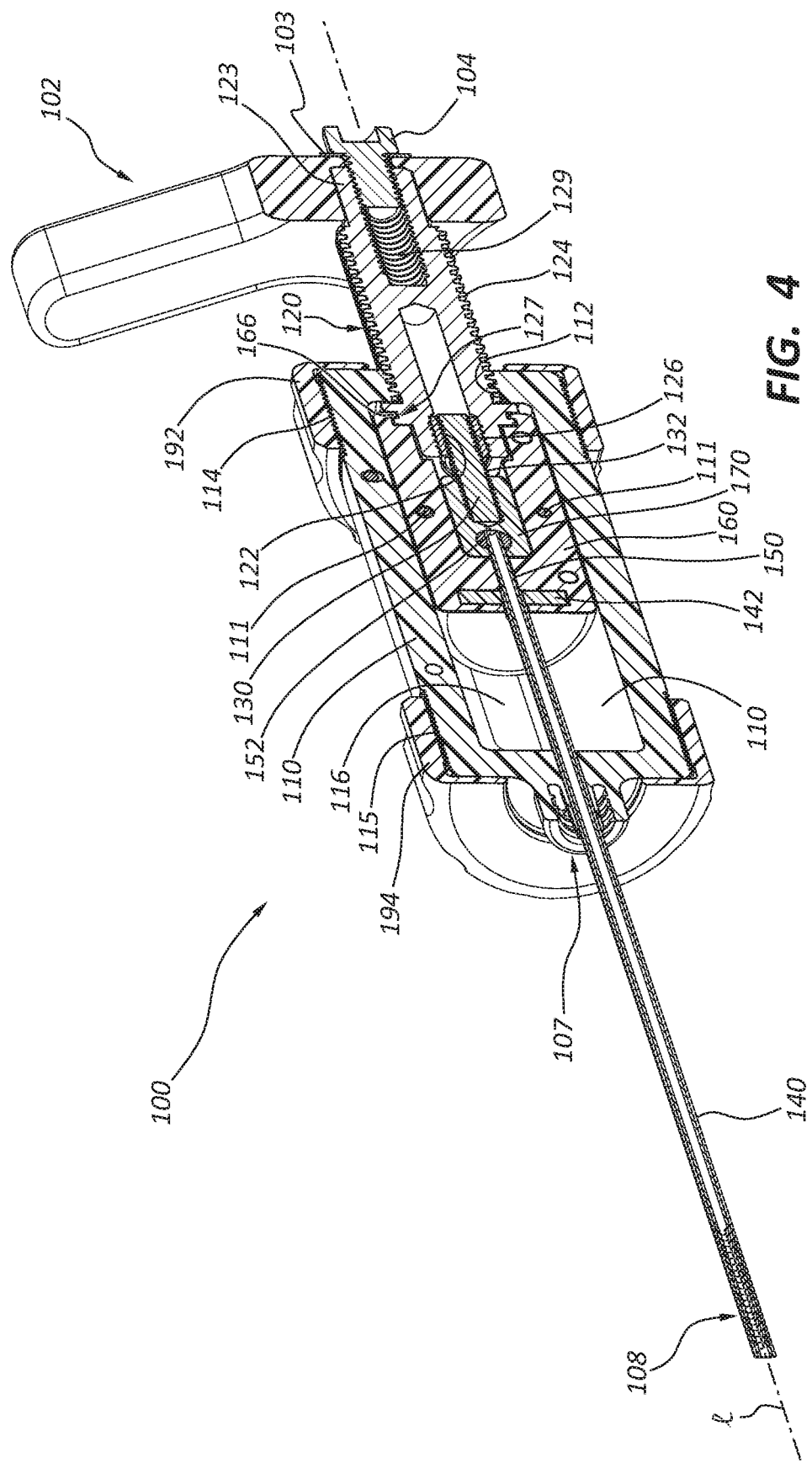
FIG. 4 is a cross-sectional perspective view of the osteotome of FIG. 1 through plane 4-4 of FIG. 1.
Figure 5:
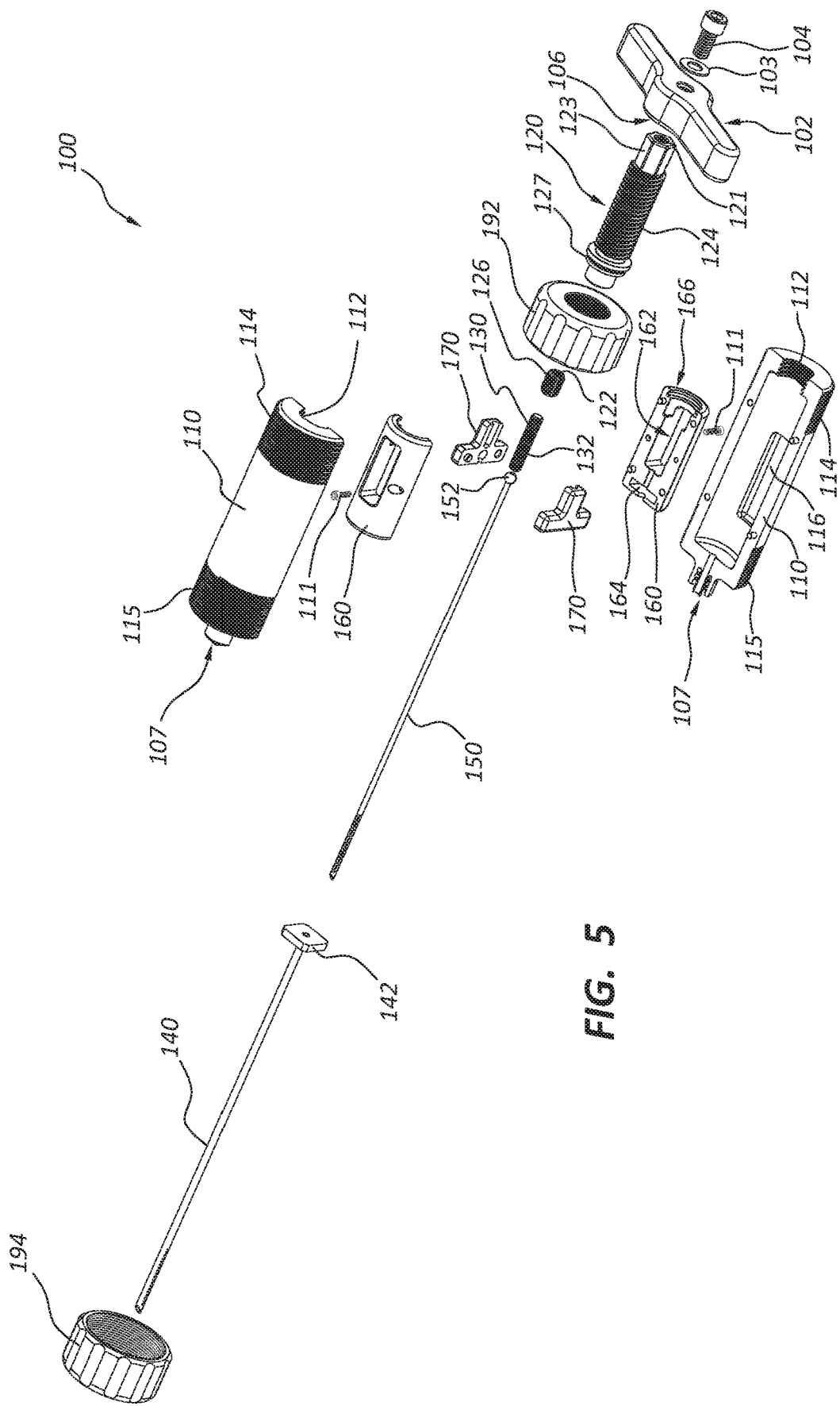
FIG. 5 is an exploded perspective view of the osteotome of FIG. 1.
Figure 6:
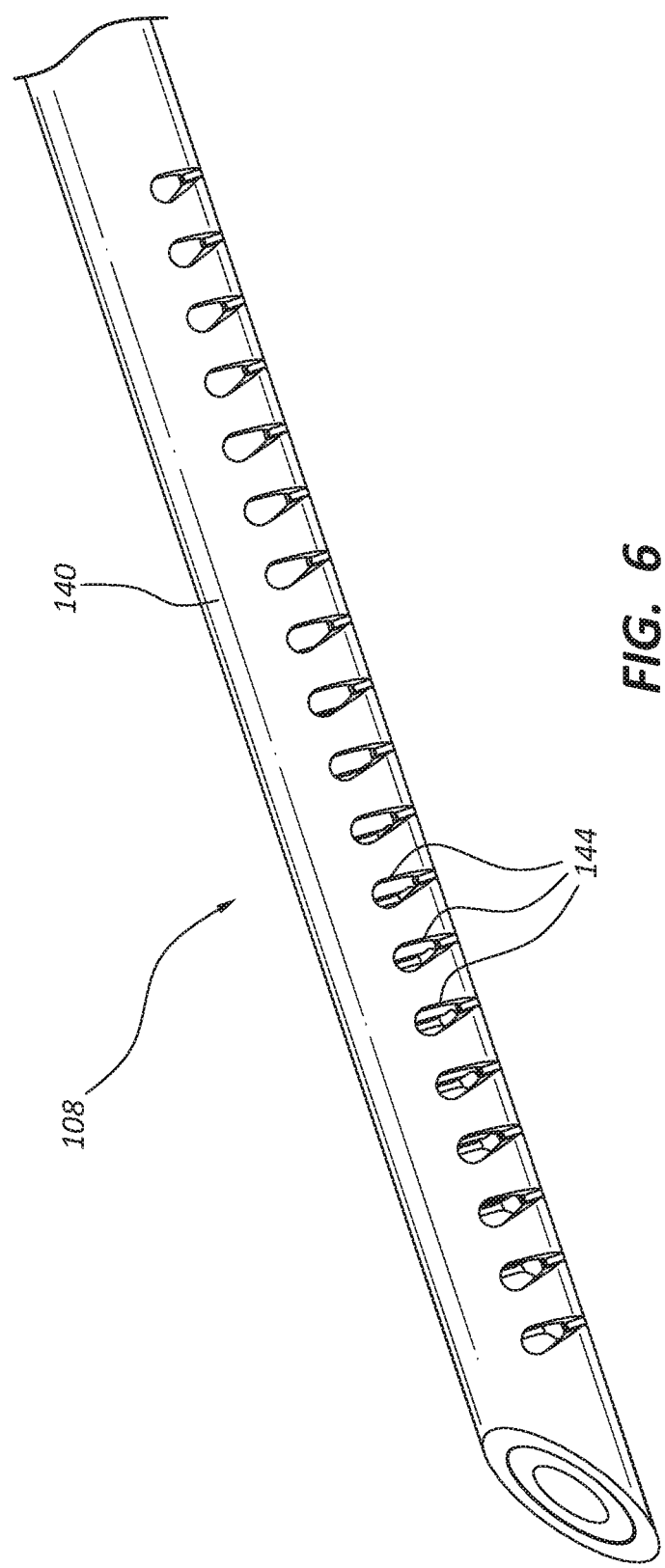
FIG. 6 is a perspective view of a distal portion of the osteotome of FIG. 1 in a fully retracted and straight configuration.
Figure 7:
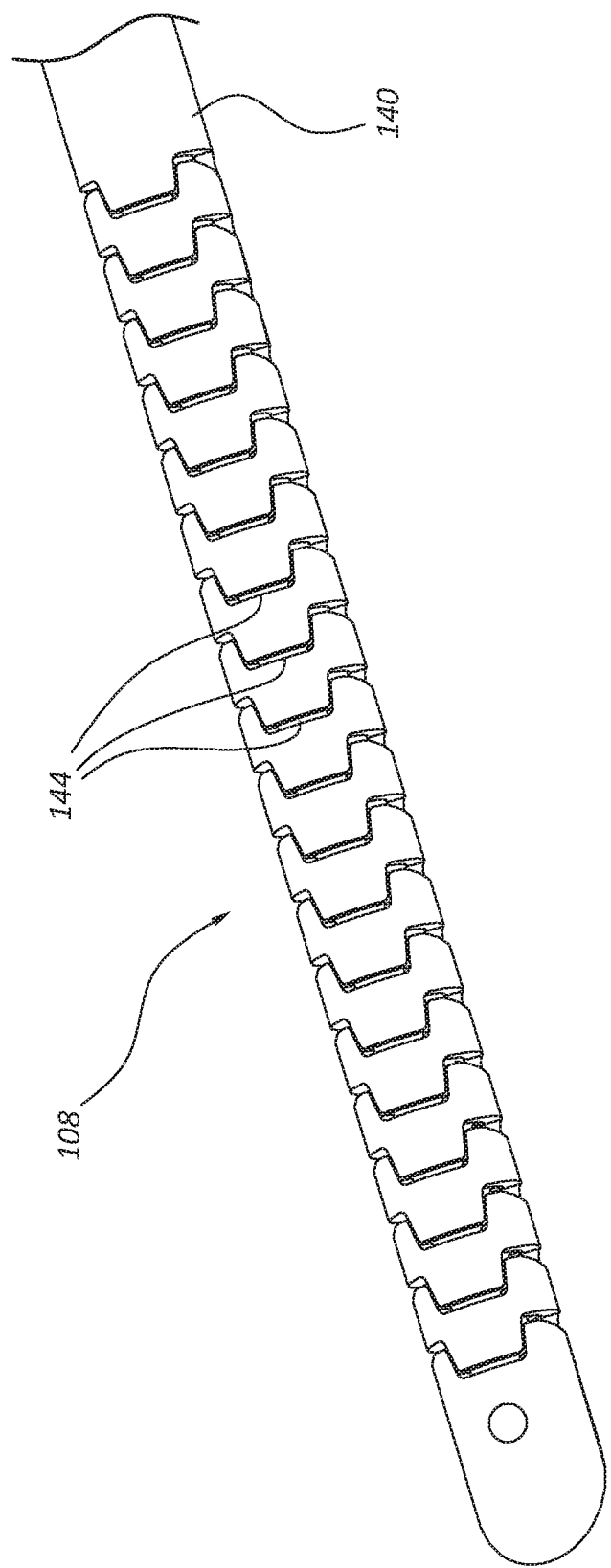
FIG. 7 is a bottom view of the distal portion of the osteotome of FIG. 1 in a fully retracted and straight configuration.
Figure 8:
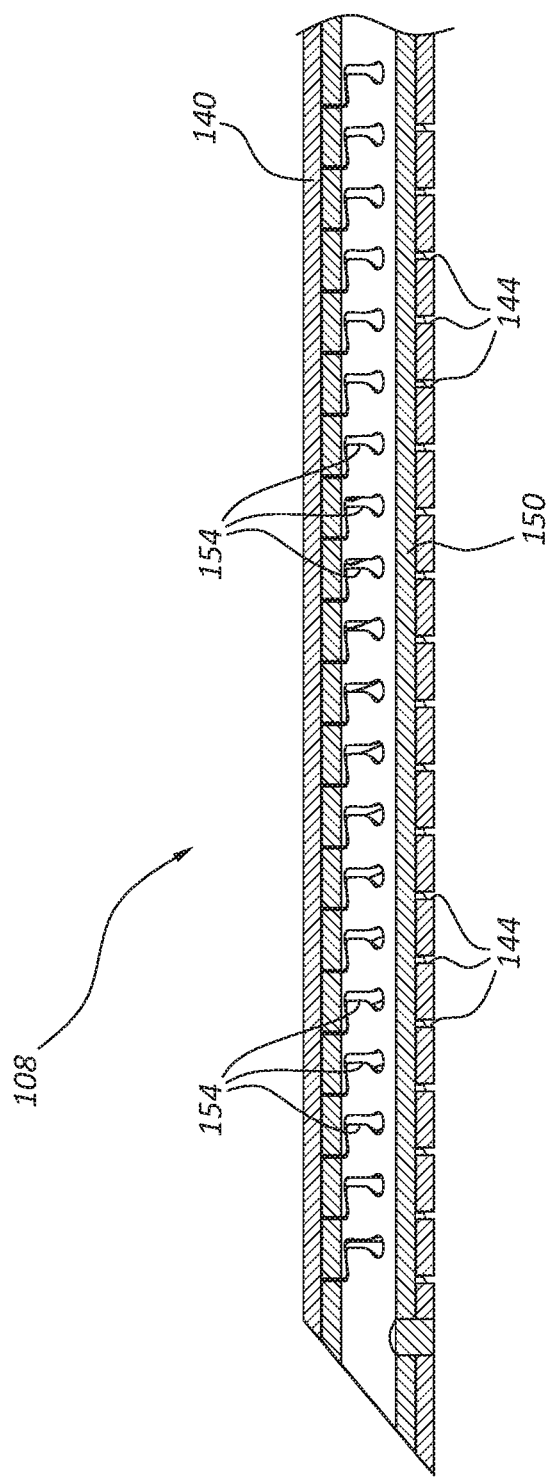
FIG. 8 is a cross-sectional side view of the distal portion of the osteotome of FIG. 1 in a fully retracted and straight configuration.
Figure 9:
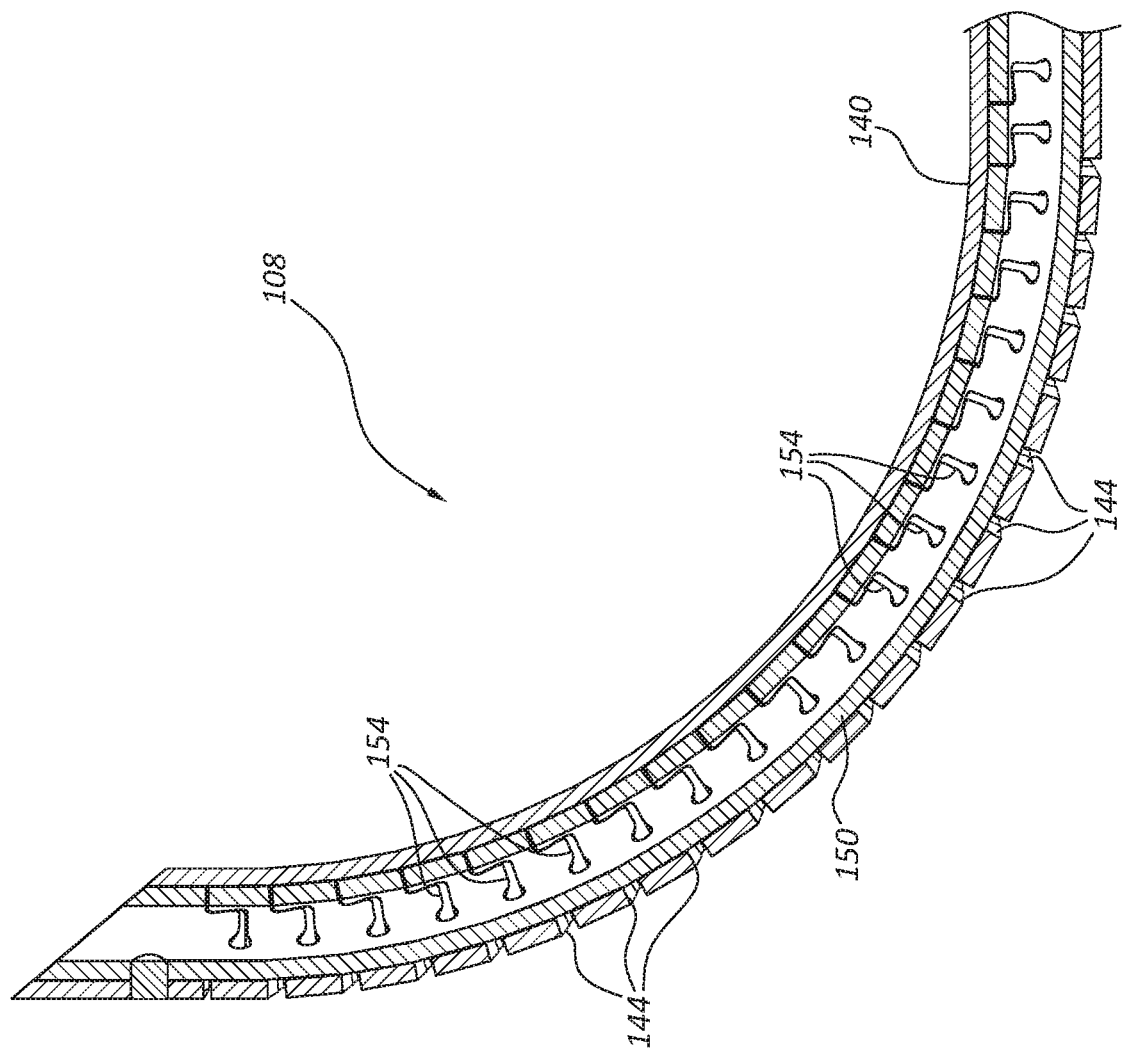
FIG. 9 is a cross-sectional side view of a distal portion of the osteotome of FIG. 1 in a fully advanced and articulated configuration.

FIGS. 1-5 provide various views of a medical device 100 (an osteotome) or portions thereof for creating or expanding a cavity within a bone of a patient. For example, FIG. 1 provides a first perspective view of the medical device 100. FIG. 2 provides a second perspective view of the medical device 100. FIG. 3 provides a first cross-sectional view of the medical device 100 through plane 3-3 of FIG. 1. FIG. 4 provides a cross-sectional perspective view of the medical device 100 through plane 4-4 of FIG. 1. FIG. 5 provides an exploded perspective view of the medical device 100. FIGS. 6-8 provide perspective (FIG. 6), bottom (FIG. 7), and cross-sectional (FIG. 8) views of a distal portion 108 of the medical device 100 in a fully retracted and straight configuration. FIG. 9 provides a side view of the distal portion 108 of the medical device 100 in a fully advanced and articulated configuration. Elements of the medical device 100 are also shown in FIGS. 10A-12B.

As shown in FIGS. 1-12B, the medical device 100 may include, among other elements, a handle 102, a housing 110, a first shaft 120, a second shaft 130, a third shaft 140, a fourth shaft 150, a shuttle 160, and a casing 170.

The handle 102 may be coupled to the first shaft 120 such that rotation of the handle 102 results in rotation of the first shaft 120. In some embodiments, the handle 102 is coupled to the first shaft 120 such that when the handle 102 is rotated, the first shaft 120 rotates at the same rate as the handle 102. Stated differently, as the handle 102 is rotated 360 degrees about a longitudinal axis (l), the first shaft 120 may also rotate 360 degrees about the longitudinal axis (l).

In the depicted embodiment, the handle 102 is coupled to the first shaft 120 by inserting a hexagonal proximal portion 123 of the first shaft 120 into a complementary hexagonal opening 106 on the handle 102. A fastener 104 (e.g., a bolt) may then be inserted through the handle 102 into a proximal opening 121 of the first shaft 120 such that the fastener 104 is threadably engaged with interior threads 129 disposed adjacent to a proximal end of the first shaft 120. In some embodiments, a washer 103 is disposed between the fastener 104 and the handle 102.

The housing 110 may be generally elongate in shape. In the depicted embodiment, the housing 110 includes interior threads 112 disposed adjacent the proximal end of the housing 110, a recess 116, a distal adaptor 107, proximal exterior threads 114, and distal exterior threads 115. The distal adaptor 107 (e.g., a male luer connection) may be configured to facilitate attachment to an introducer that has been inserted into a patient. The housing may encompass or partially encompass various components, such as the shuttle 160, the casing 170, and the second shaft 130.

In some embodiments, the housing 110 is formed from two separate portions (see FIG. 5) that are attached to one another. For example, in some embodiments, the medical device 100 includes one or more threaded caps 192, 194 that secure a first portion of the housing 110 to a second portion of the housing 110. A proximal threaded cap 192 may be configured to threadably engage with the proximal exterior threads 114, while a distal threaded cap 194 may be configured to threadably engage with the distal exterior threads 115 of the housing 110. The interaction between the threaded caps 192, 194 and the exterior threads 114, 115 of the housing 110 may secure a first portion of the housing 110 to the second portion of the housing 110.

The first shaft 120 may include exterior threads 124. The exterior threads 124 may theadably engage with the interior threads 112 of the housing 110 such that the first shaft 120 is threadably coupled to the housing 110. Due to the threaded interaction between the first shaft 120 and the housing 110, rotation of the handle 102 in a first (e.g., clockwise) direction may cause simultaneous rotation of the first shaft 120, thereby distally displacing the first shaft 120 with respect to the housing 110. As discussed below, the exterior threads 124 may have a pitch that is greater than the pitch of exterior threads 132 on the second shaft 130. In some embodiments, the exterior threads 124 of the first shaft 120 form a right-handed helix.

The first shaft 120 may be coupled to the shuttle 160 that is disposed within the housing 110. For example, the shuttle 160 may be rotatably (but not threadedly) coupled to the first shaft 120 such that rotation of the first shaft 120 in a first (e.g., clockwise) direction with respect to the housing 110 results in axial displacement of the shuttle 160 relative to the housing 110. More particularly, an inward-projecting ridge 166 adjacent the proximal end of the shuttle 160 may be disposed within an exterior slot 127 of the first shaft 120 such that axial displacement of the first shaft 120 results in an equal magnitude of axial displacement of the shuttle 160. In some embodiments, the shuttle 160 is formed from two separate components (e.g., halves) that are attached to one another, such as via screws 111.

The shuttle 160 may further include an aperture 162. The aperture 162 may be configured to permit extension of an arm of the casing 170 through the shuttle 160 for interaction with a recess 116 of the housing 110 as described in further detail below. The shuttle 160 may also include one or more recesses 164 that are designed to accommodate (e.g., secure) an anchor 142 at the proximal end of the third shaft 140. The shuttle 160 may be configured to travel back and forth within the housing 110 along the longitudinal axis of the medical device 100.

In some embodiments, the first shaft 120 further includes an inner sleeve 126 disposed adjacent to the distal end of the first shaft 120. The inner sleeve 126 may be coupled to the remainder of the first shaft 120 such that the inner sleeve 126 and the first shaft 120 rotate at the same rate. In other words, the inner sleeve 126 may be fixedly coupled to a remainder of the first shaft 120. The inner sleeve 126 may have a composition that differs from the composition of the remainder of the first shaft 120. For example, in some embodiments, the inner sleeve 126 is formed from a metal or metal alloy, while the remainder of the first shaft 120 is formed from a synthetic polymer (e.g., a plastic). The composition of the inner sleeve 126 may provide increased durability relative to the composition of the remainder of the first shaft 120. In other embodiments, there is no separate inner sleeve 126.

The first shaft 120 may further include interior threads 122 that are disposed adjacent the distal end of the first shaft 120. In the depicted embodiment, the interior threads 122 are disposed on an interior of the inner sleeve 126.

The second shaft 130 may be threadably coupled to the first shaft 120. For example, in the depicted embodiment, the interior threads 122 adjacent the distal end of the first shaft 120 may threadably engage with the exterior threads 132 of the second shaft 130. The interior threads 122 of the first shaft 120 and the exterior threads 132 of the second shaft 130 may each have a shorter pitch than the exterior threads 124 of the first shaft 120 and the interior threads 112 of the housing 110. In some embodiments, the exterior threads 132 of the second shaft 130 form a right-handed helix.

As the first shaft 120 is rotated in a first (e.g., clockwise) direction, the second shaft 130 may be prevented from rotating about the longitudinal axis (l) of the medical device by the casing 170 described in greater detail below. Thus, rotation of the first shaft 120 in a first direction may cause the first shaft 120 to move distally with respect to the second shaft 130 due to the difference in pitch between the threads 122, 132, and the threads 124, 112. Thus, rotation of the first shaft 120 with respect to the housing 110 may result in axial displacement of the casing 170 relative to the shuttle 160.

As shown in FIG. 5, in some embodiments, the casing 170 is generally T-shaped. The casing 170 may be formed from two separate components (e.g., halves) that are attached to one another. In some embodiments, a proximal portion of the casing 170 is fixedly coupled to the second shaft 130 (e.g., via an adhesive). A distal portion of the casing 170 may be coupled to a proximal end of the fourth shaft 150. For example, the casing 170 may be formed by attaching a first half of the casing 170 that includes a hemisphere-shaped indentation with a second half of the casing 170 that includes another hemisphere-shaped indentation. The indentations on each half of the casing 170 may cooperate to form a pocket (e.g., a spherical pocket) that accommodates a bulbous proximal end 152 (e.g., a spherical ball) of the fourth shaft 150. Due to this interaction, the proximal end 152 of the fourth shaft 150 may be axially displaced with the casing 170 as described in greater detail below. Stated differently, the proximal end 152 of the fourth shaft 150 may move with the casing 170 along the longitudinal axis (l) of the medical device 100.

The casing 170 may include one or more arms that are configured to interact with one or more recesses 116 within the housing 110. For example, in some embodiments, each arm of the T-shaped casing 170 may extend though an aperture 162 in the shuttle 160 to the recess 116 within the housing 110. The recess(es) 116 of the housing 110 may interact with the casing 170 to prevent rotation of both the casing 170 and the second shaft 130 relative to the housing 110.

The third shaft 140 may be a metallic shaft that extends from a proximal anchor 142 that is disposed (e.g., secured) within the recess(es) 164 of the shuttle 160 to a position at or adjacent to the distal end of the medical device 100. The third shaft 140 may include an elongate lumen that extends from a proximal opening in the anchor 142 to adjacent the distal end of the medical device 100. In some embodiments, the third shaft 140 may include a plurality of slots 144 (see FIGS. 6-9) adjacent its distal end.

The fourth shaft 150 may be a metallic shaft that extends distally from the bulbous proximal end 152 within the casing 170 to a position at or adjacent to the distal end of the medical device 100. In some embodiments, the fourth shaft 150 includes an elongate lumen. Like the third shaft 140, the fourth shaft 150 may include a plurality of slots 154 adjacent its distal end. In some embodiments, the slots 154 may be disposed opposite the slots 144 of the third shaft 140.

The fourth shaft 150 may be at least partially disposed within an elongate lumen of the third shaft 140. Stated differently, the third shaft 140 may be disposed around a distal portion of the fourth shaft 150.

The third shaft 140 and the fourth shaft 150 may together form an articulating distal portion 108 of the medical device 100. As shown in FIGS. 8 and 9, the fourth shaft 150 may be attached (e.g., welded) to the third shaft 140 at a position that is adjacent to a distal end of the third shaft 140 while the remainder of the fourth shaft 150 is unattached from the third shaft 140. In other words, a proximal portion of the fourth shaft 150 may be longitudinally displaceable relative to the third shaft 140. By displacing the proximal end of the fourth shaft 150 relative to the third shaft 140 as described in greater detail below, the articulating distal portion 108 of the medical device 100 may be displaced. More specifically, by displacing the proximal end of the fourth shaft 150 relative to the third shaft 140, the distal portion of the medical device 100 may transition from a linear configuration (FIGS. 6-8) to a non-linear configuration (FIG. 9) and vice versa.

Figure 11A:
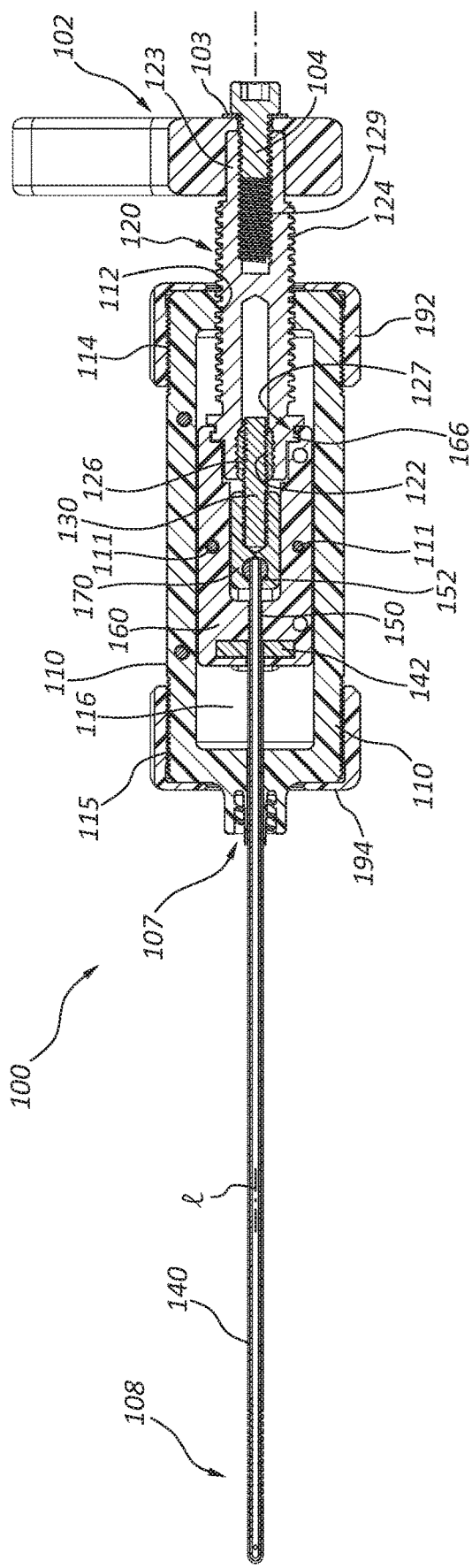
FIG. 11A is a cross-sectional view of the osteotome of FIG. 1 in a second configuration.
Figure 11B:
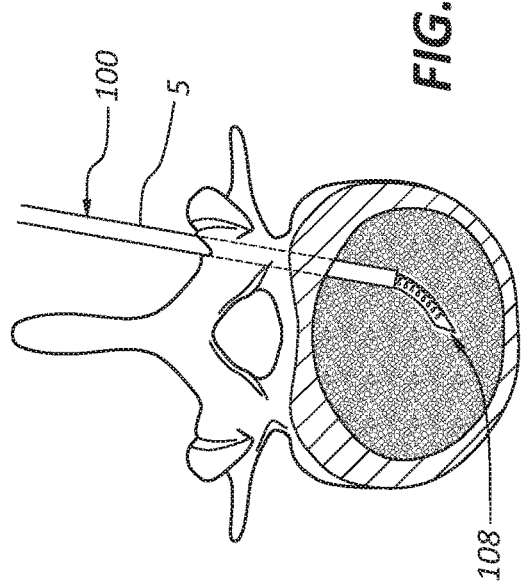
FIG. 11B depicts the osteotome of FIG. 1 in a vertebra of the patient when the osteotome is in the second configuration.

The medical device 100 may be used in one or more medical procedures, such as procedures for creating or expanding a cavity within bone of a patient. Various stages of an exemplary procedure for creating or expanding a cavity within bone of a patient are shown in FIGS. 10A-12B. More particularly, FIG. 10A discloses a cross-sectional view of the medical device 100 in a first configuration. FIG. 10B shows the medical device 100 in the first configuration where the medical device 100 is at least partially disposed within an introducer 5. FIGS. 11A and 11B are analogous to FIGS. 10A and 10B, except that the medical device 100 is in a second configuration. FIGS. 12A and 12B similarly show the medical device 100 in a third configuration.

An exemplary medical procedure may involve obtaining a medical device, such as the medical device 100 (e.g., an osteotome) and inserting a distal region (e.g., a pointed distal tip) of the medical device 100 into bone of a patient. For instance, in some embodiments, a distal region of the medical device 100 is inserted through an introducer 5 into a vertebral body (see FIG. 10B) of a patient (e.g., a sedated human patient in the prone position). In some embodiments, the housing 110 of the medical device 100 may be coupled (e.g., attached) to the introducer 5 via the distal adaptor 107 prior to rotating the handle 102 and/or the first shaft 120 of the medical device 100 relative to the housing 110.

Once the distal end of the medical device 100 is disposed within bone of the patient (e.g., as shown in FIG. 10B), the practitioner may rotate the handle 102 about the longitudinal axis (l) of the medical device 100 in a first (e.g., clockwise) direction). Due to the interaction of the handle 102 with the first shaft 120, such manipulation of the handle 102 of the medical device 100 causes rotation of the first shaft 120 relative to the housing 110. Rotation of the first shaft 120 relative to the housing 110 causes the first shaft 120 to be displaced in a distal direction relative to the housing 110 due to the interaction of the exterior threads 124 of the first shaft 120 with the interior threads 112 adjacent the proximal end of the housing 110.

Due to the interaction between the inward-projecting ridge 166 of the shuttle 160 and the exterior slot 127 of the first shaft 120, rotation of the first shaft 120 also causes the shuttle 160 to move distally with the first shaft 120 along the longitudinal axis (l) of the medical device 100. Stated differently, as a result of rotational input at the handle 102, the first shaft 120 and the shuttle 160 may move distally within the housing 110 at the same rate. In the depicted embodiment, the shuttle 160 does not rotate within the housing 110 about the longitudinal axis (l) of the medical device 100. Rather, because (1) the casing 170 does not rotate relative to the housing 110 due to the interaction between arms of the casing 170 and the recess 116 within the housing 110 and (2) rotation of the shuttle 160 is constrained by the casing 170, the shuttle 160 of the depicted embodiment cannot rotate about the longitudinal axis (l) of the medical device 100. Stated differently, rotation of the first shaft 120 relative to the housing 110 causes rotation of the inward-projecting ridge 166 within the exterior slot 127 of the first shaft 120.

Furthermore, as the proximal anchor 142 of the third shaft 140 is disposed within the recess 164 of the shuttle 160, the proximal portion of the third shaft 140 moves distally with both first shaft 120 and the housing 110. Stated differently, each of the first shaft 120, the shuttle 160, and the proximal portion third shaft 140 may move axially (e.g., distally) relative to the housing 110 at a first rate. In other words, the shuttle 160 and the third shaft 140 may be coupled to the first shaft 120 such that axial displacement of the first shaft 120 a first distance relative to the housing 110 results in axial displacement of the third shaft 140 and the shuttle 160 a distance relative to the housing 110 that is equal to the first distance.

Additionally, as the first shaft 120 is rotated relative to the housing 110, the interior threads 122 adjacent the distal end of the first shaft 120 may interact with the exterior threads 132 of the second shaft 130. More specifically, as the first shaft 120 is rotated relative to the housing 110, the first shaft 120 may be distally displaced relative to the second shaft 130 due to the interaction between the interior threads 122 of the first shaft 120 and the exterior threads 132 of the second shaft 130. Like the shuttle 160, the second shaft 130 in the depicted embodiment does not rotate within the housing 110 about the longitudinal axis (l) of the medical device 100. Rather, the second shaft 130 is fixedly coupled to the casing 170 and is thereby rotationally constrained within the housing 110. Thus, as a result of being rotationally constrained in this manner, rotation of the first shaft 120 causes the second shaft 130 to move proximally relative to the first shaft 120. Further, as the pitch of the exterior threads 124 of the first shaft 120 and the interior threads 112 of the housing 110 is greater than the pitch of the interior threads 122 and the exterior threads 132, the first shaft 120 may move both (1) proximally relative to the shuttle 160 and (2) distally relative to the housing 110. Stated differently, as the handle 102 is rotated, the second shaft 130 may move distally within the housing 110 at a second rate that is different (e.g., slower) than the first rate at which the first shaft 120, the shuttle 160, and/or the proximal portion of the third shaft 140 move distally within the housing 110. In this manner, the fourth shaft 150 may be coupled to the second shaft 130 such that axial displacement of the second shaft 130 a second distance relative to the housing 110 results in axial displacement of the fourth shaft 150 a distance relative to the housing 110 that is equal to the second distance.

As (1) the casing 170 is fixedly coupled to the second shaft 130 and (2) the fourth shaft 150 is coupled to the casing 170 due to the position of the bulbous proximal end 152 within the pockets of the casing 170, the casing 170 and the proximal portion of the fourth shaft 150 may move axially (e.g., distally) with the second shaft. Stated differently, the second shaft 130 and the fourth shaft 150 may move distally within the housing 110 at a second rate that is slower than the rate at which both the first shaft 120 and the proximal portion of the third shaft 140 move distally with respect to the housing 110.

As the proximal portion of the third shaft 140 moves distally with respect to the housing 110 at a rate that is greater than the rate at which the fourth shaft 150 moves distally with respect to the housing 110, a distal portion of the medical device 100 may transition from a linear configuration (FIGS. 6-8) to a non-linear configuration (FIG. 9).

For example, as the distance between the proximal anchor 142 of the third shaft 140 and the proximal bulbous end 152 of the fourth shaft 150 increases, the distal tip of the medical device 100 may be simultaneously displaced both (1) distally relative to the housing 110 and (2) laterally relative to the longitudinal axis of the medical device 100. Stated differently, as a result of rotation of the first shaft 120 relative to the housing 110, (1) the distal portion 108 of the medical device 100 may be articulated such that a distal tip of the medical device 100 is laterally displaced relative to a longitudinal axis (l) of the medical device 100 and (2) the distal portion 108 of the medical device 100 is displaced in an axial (e.g., distal) direction relative to the housing 110.

In the depicted embodiment, as the first shaft 120 is rotated relative to the housing 110, the distal portion 108 of the medical device 100 may transition from a linear configuration to a non-linear configuration such that (1) the slots 144 on the third shaft 140 are disposed on a concave side of a bend and (2) the slots 154 on the fourth shaft 150 are disposed on a convex side of the bend (see FIG. 9). From the perspective shown in FIGS. 10A, 11A, and 12A, the distal tip of the medical device 100 may be displaced away from the longitudinal axis and into the page. The transition from the linear configuration to the non-linear configuration may occur in a single plane. Stated differently, in some embodiments, movement of the distal portion 108 of the medical device 100 is limited to a single plane. By rotating the handle 102 and the first shaft 120 a selected amount, the articulating distal portion 108 may be bent to a selected degree.

In some embodiments, the process described above is reversible. Stated differently, the medical device 100 may transition from the non-linear configuration to the linear configuration by rotating the handle 102 and/or the first shaft 120 in a second direction (e.g., counterclockwise) that differs from the first direction.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A medical device for creating or expanding a cavity within bone of a patient, the medical device comprising:
   a housing;
   a first shaft that is threadably coupled to the housing;
   a second shaft that is threadably coupled to the first shaft;

a third shaft that is coupled to the first shaft such that a proximal portion of the third shaft moves axially with the first shaft; and a fourth shaft that is coupled to the second shaft such that a proximal portion of the fourth shaft moves axially with the second shaft;

wherein the medical device is configured such that rotation of the first shaft relative to the housing in a first direction results in simultaneous displacement of a distal tip of the medical device in a distal direction relative to the housing and displacement of the distal tip of the medical device in a direction that is lateral to a longitudinal axis of the medical device, and wherein the medical device is configured such that rotation of the first shaft relative to the housing results in (1) axial displacement of the first shaft and the proximal portion of the third shaft relative to the housing at a first rate and (2) axial displacement of the second shaft and the fourth shaft relative to the housing at a second rate that is different from the first rate.

2. The medical device of claim 1, wherein the second shaft is coupled to the housing to prevent rotation of the second shaft relative to the housing.

3. The medical device of claim 1, wherein:
the first shaft comprises exterior threads that threadably engage threads of the housing; and
the second shaft comprises exterior threads that threadably engage with interior threads of the first shaft;
wherein the exterior threads of the first shaft have a pitch that is greater than a pitch of the exterior threads of the second shaft.

4. The medical device of claim 3, wherein:
the exterior threads of the first shaft form a right-handed helix; and
the exterior threads of the second shaft form a right-handed helix.

5. The medical device of claim 1, wherein the fourth shaft is at least partially disposed within an elongate lumen of the third shaft.

6. The medical device of claim 1, further comprising a handle that is coupled to the first shaft such that rotation of the handle results in rotation of the first shaft.

7. The medical device of claim 1, further comprising:
a casing that is fixedly coupled to the second shaft and a proximal end of the third shaft; and
a shuttle that is rotatably, but not threadably, coupled to the first shaft, wherein the shuttle is disposed within the housing;
wherein rotation of the first shaft with respect to the housing results in axial displacement of the casing relative to the shuttle.

8. The medical device of claim 7, wherein the housing comprises one or more recesses that interact with the casing to prevent rotation of the second shaft relative to the housing.

9. The medical device of claim 1, wherein the housing comprises an adaptor that is configured to facilitate attachment of the housing to an introducer.

10. The medical device of claim 1, wherein:
a proximal portion of the fourth shaft is longitudinally displaceable relative to the third shaft; and
the fourth shaft is attached to the third shaft at a position that is adjacent a distal end of the third shaft.

11. An osteotome comprising:
a housing;
a first shaft that is threadably coupled to the housing;
a second shaft that is threadably coupled to the first shaft;
a third shaft that is coupled to the first shaft such that axial displacement of the first shaft a first distance relative to the housing results in axial displacement of the third shaft a distance relative to the housing that is equal to the first distance;
a fourth shaft that is at least partially disposed within an elongate lumen of the third shaft, wherein the fourth shaft is coupled to the second shaft such that axial displacement of the second shaft a second distance relative to the housing results in axial displacement of the fourth shaft a distance relative to the housing that is equal to the second distance; and
a distal portion of the osteotome, the distal portion comprising both a portion of the third shaft and a portion of the fourth shaft;
wherein rotation of the first shaft relative to the housing simultaneously causes (1) axial displacement of the first shaft relative to the housing at a first rate, (2) axial displacement of the second shaft relative to the housing at a second rate that is different from the first rate, and (3) articulation of the distal portion such that a distal tip of the osteotome is laterally displaced relative to a longitudinal axis of the osteotome.

12. The osteotome of claim 11, wherein rotation of the first shaft relative to the housing causes displacement of the distal portion in an axial direction relative to the housing.

13. The osteotome of claim 11, wherein:
the first shaft comprises exterior threads that threadably engage with interior threads of the housing; and
the second shaft comprises exterior threads that threadably engage with interior threads of the first shaft;
wherein the exterior threads of the first shaft have a pitch that is greater than a pitch of the exterior threads of the second shaft.

14. A method of manipulating an osteotome, the method comprising:
obtaining the osteotome of claim 11;
inserting a distal portion of the osteotome into bone of a patient; and
rotating the first shaft of the osteotome relative to the housing.

15. The method of claim 14, wherein inserting the distal portion of the osteotome into bone of the patient comprises inserting the distal portion of the osteotome through an introducer.

16. The method of claim 15, further comprising coupling the housing to the introducer prior to rotating the first shaft of the osteotome relative to the housing.

17. The method of claim 14, wherein the bone of the patient is a human vertebra.

* * * * *